(12) United States Patent
Suzuki et al.

(10) Patent No.: US 11,253,226 B2
(45) Date of Patent: Feb. 22, 2022

(54) ULTRASONIC IMAGING DEVICE, METHOD FOR ADJUSTING INTER-TRANSMISSION WEIGHT, AND ULTRASONIC IMAGING METHOD

(71) Applicant: Hitachi, Ltd., Tokyo (JP)

(72) Inventors: Mayumi Suzuki, Tokyo (JP); Teiichiro Ikeda, Tokyo (JP); Hiroshi Masuzawa, Tokyo (JP); Chizue Ishihara, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 1047 days.

(21) Appl. No.: 15/550,151

(22) PCT Filed: Jan. 25, 2016

(86) PCT No.: PCT/JP2016/052031
§ 371 (c)(1),
(2) Date: Aug. 10, 2017

(87) PCT Pub. No.: WO2016/129376
PCT Pub. Date: Aug. 18, 2016

(65) Prior Publication Data
US 2018/0021013 A1 Jan. 25, 2018

(30) Foreign Application Priority Data
Feb. 12, 2015 (JP) .............................. JP2015-025103

(51) Int. Cl.
*A61B 8/14* (2006.01)
*G01S 7/52* (2006.01)
(Continued)

(52) U.S. Cl.
CPC .............. *A61B 8/14* (2013.01); *A61B 8/4488* (2013.01); *A61B 8/54* (2013.01); *G01S 7/52033* (2013.01);
(Continued)

(58) Field of Classification Search
None
See application file for complete search history.

(56) References Cited

U.S. PATENT DOCUMENTS 6,685,645 B1 2/2004 McLaughlin et al.
8,485,977 B2 7/2013 Hirama
(Continued)

FOREIGN PATENT DOCUMENTS

JP 8289891 A 11/1996
JP 10277042 A 10/1998
(Continued)

OTHER PUBLICATIONS

International Search Report of PCT/JP2016/052031 dated Mar. 8, 2016.
(Continued)

*Primary Examiner* — Pascal M Bui Pho
*Assistant Examiner* — Marjan Saboktakin
(74) *Attorney, Agent, or Firm* — Mattingly & Malur, PC

(57) ABSTRACT

In performing aperture synthesis according to an ultrasound imaging apparatus, the amount of spatial change of amplification factors of phasing signals at respective receive phasing points are reduced, and a high-quality image is obtained. In a receive beamformer that generates an inter-transmission weight in accordance with a phasing range, and performs aperture synthesis processing, the inter-transmission weight being generated is applied to the receive phasing points within the phasing range obtained through transmission and reception, and the inter-transmission synthesis is performed. The inter-transmission weight is generated in such a manner that a variation form of the amplification factor between adjacent receive phasing points is smoothed and a difference of the amplification factor is reduced, as to each receive phasing point after the inter-transmission synthesis is performed.

13 Claims, 20 Drawing Sheets

(51) Int. Cl.
*A61B 8/00* (2006.01)
*G01S 15/89* (2006.01)

(52) U.S. Cl.
CPC ...... *G01S 15/8915* (2013.01); *G01S 15/8997* (2013.01)

(56) References Cited

U.S. PATENT DOCUMENTS

| | | | |
|---|---|---|---|
| 2009/0326377 A1 | 12/2009 | Hirama | |
| 2014/0198621 A1* | 7/2014 | Kim | B06B 1/0633 367/138 |
| 2015/0025385 A1* | 1/2015 | Ikeda | G01S 15/8915 600/443 |
| 2016/0054435 A1* | 2/2016 | Kim | G01S 15/8915 367/7 |
| 2016/0120503 A1* | 5/2016 | Tsushima | A61B 8/5207 367/7 |

FOREIGN PATENT DOCUMENTS

| | | |
|---|---|---|
| JP | 2009240700 A | 10/2009 |
| WO | 2014/109392 A1 | 7/2014 |
| WO | 2015/025655 A1 | 2/2015 |

OTHER PUBLICATIONS

International Preliminary Report on Patentability received in corresponding International Application No. PCT/JP2016/052031 dated Aug. 24, 2017.
Extended European Search Report received in corresponding European Application No. 16749021.8 dated Sep. 14, 2018.

* cited by examiner

Fig.4
(a) 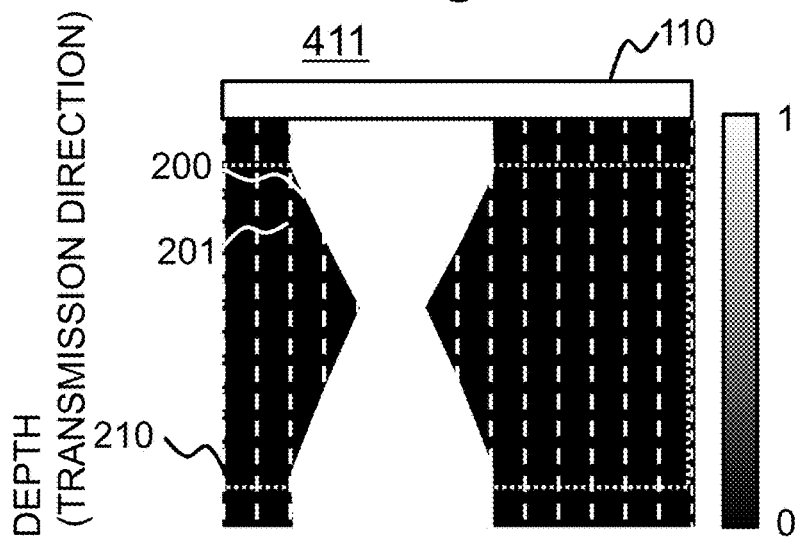
(b) 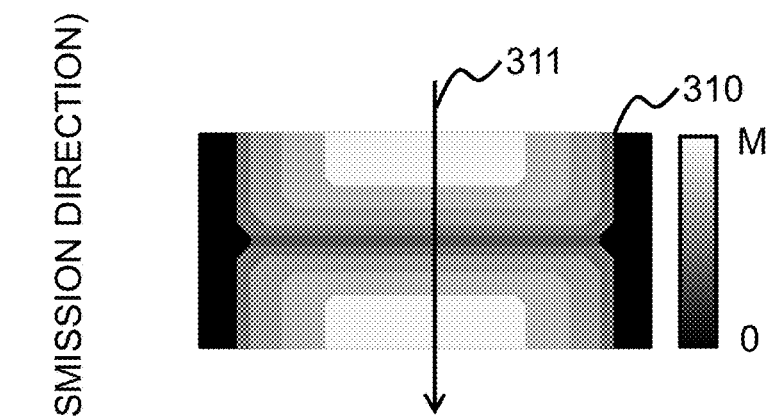
(c) 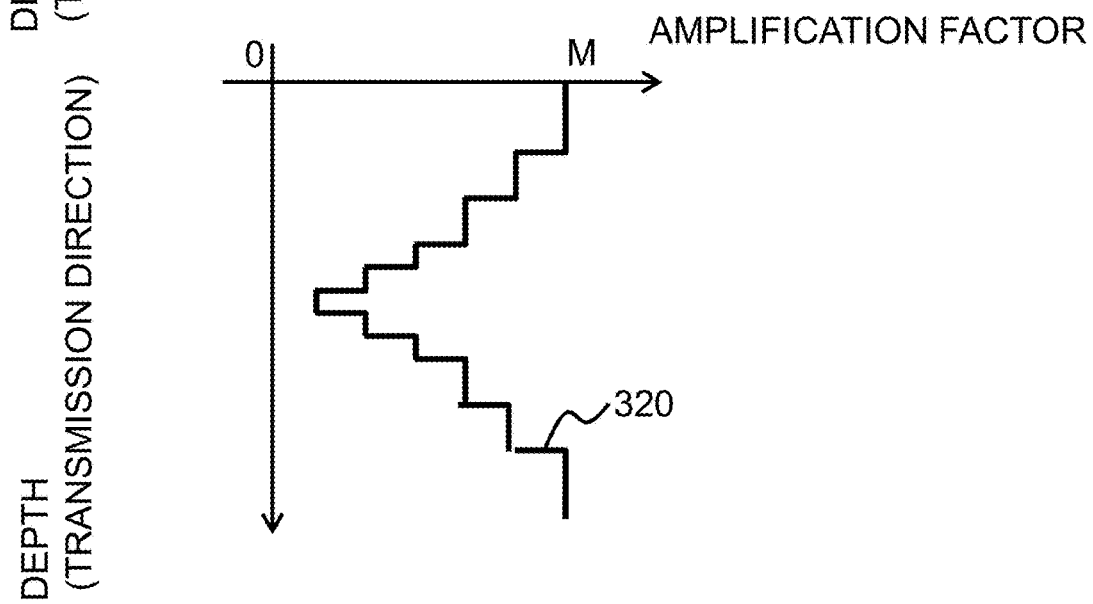

Fig.12
(a)
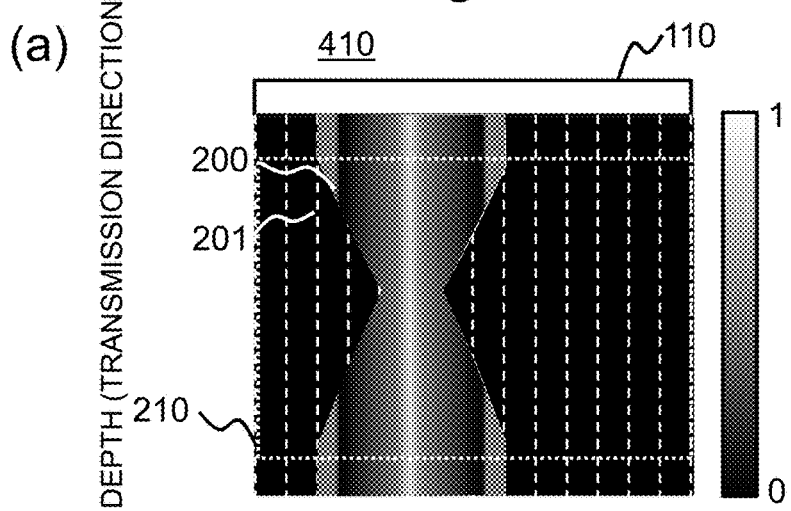
(b)
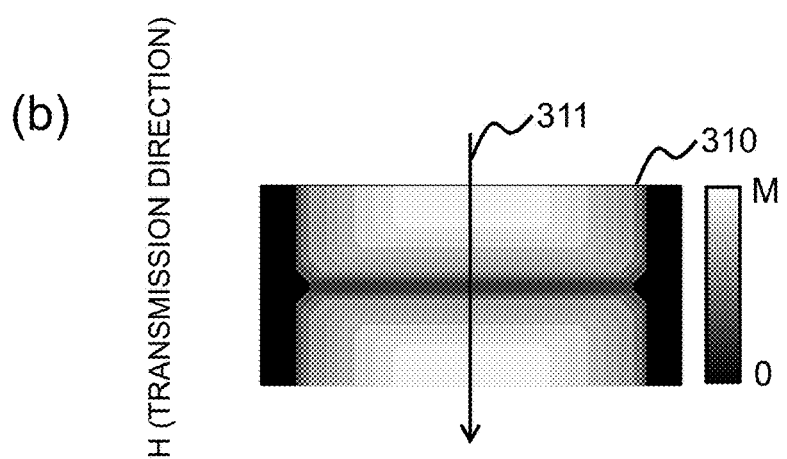
(c)
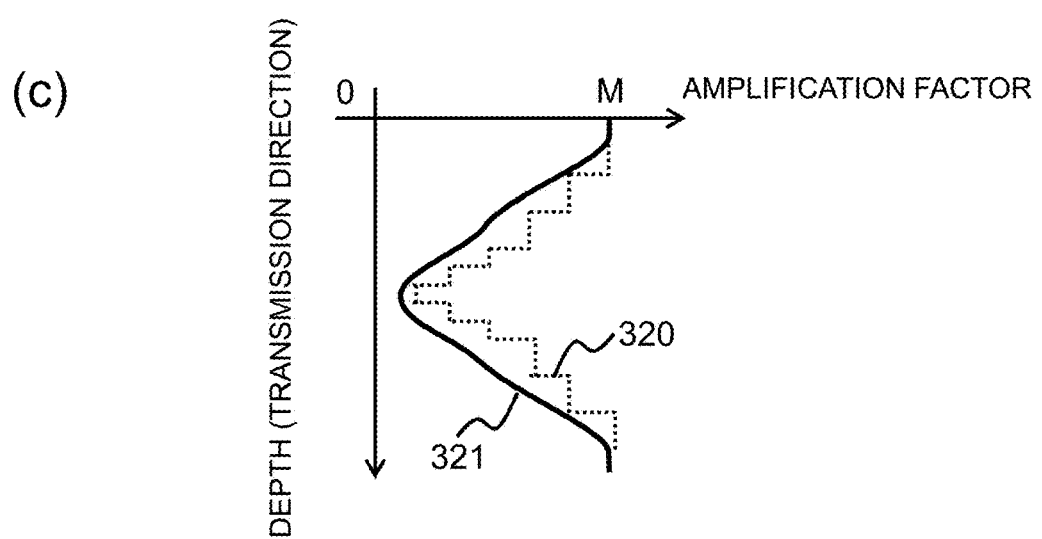

Fig.18
(a)
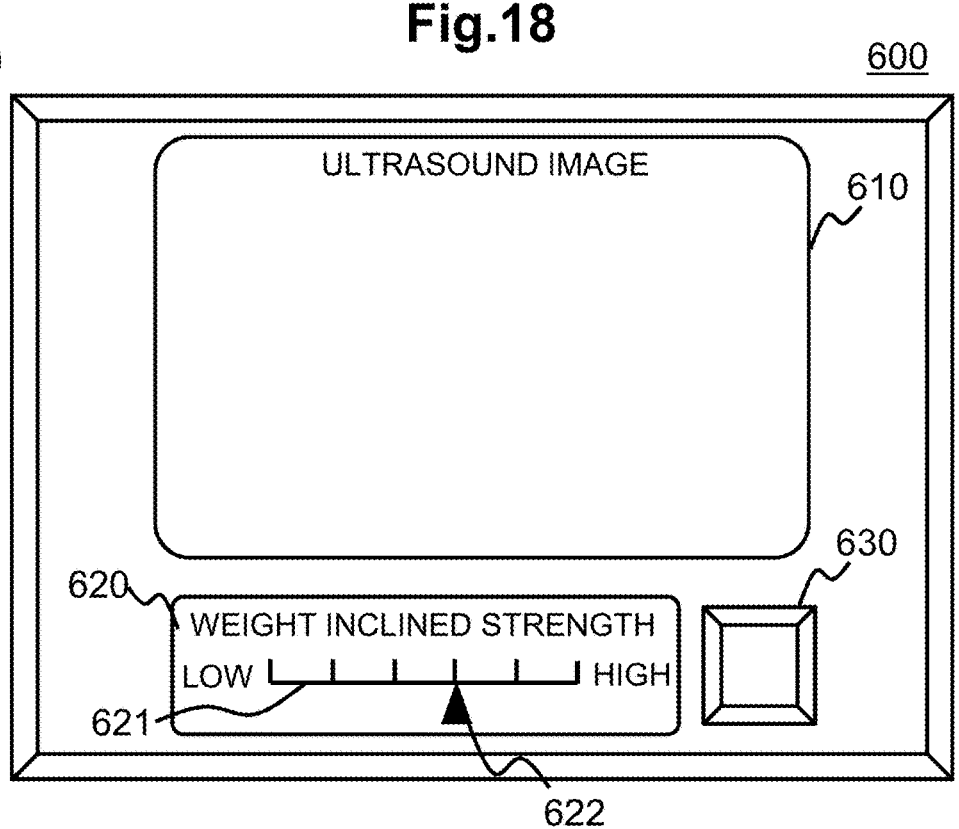
(b)
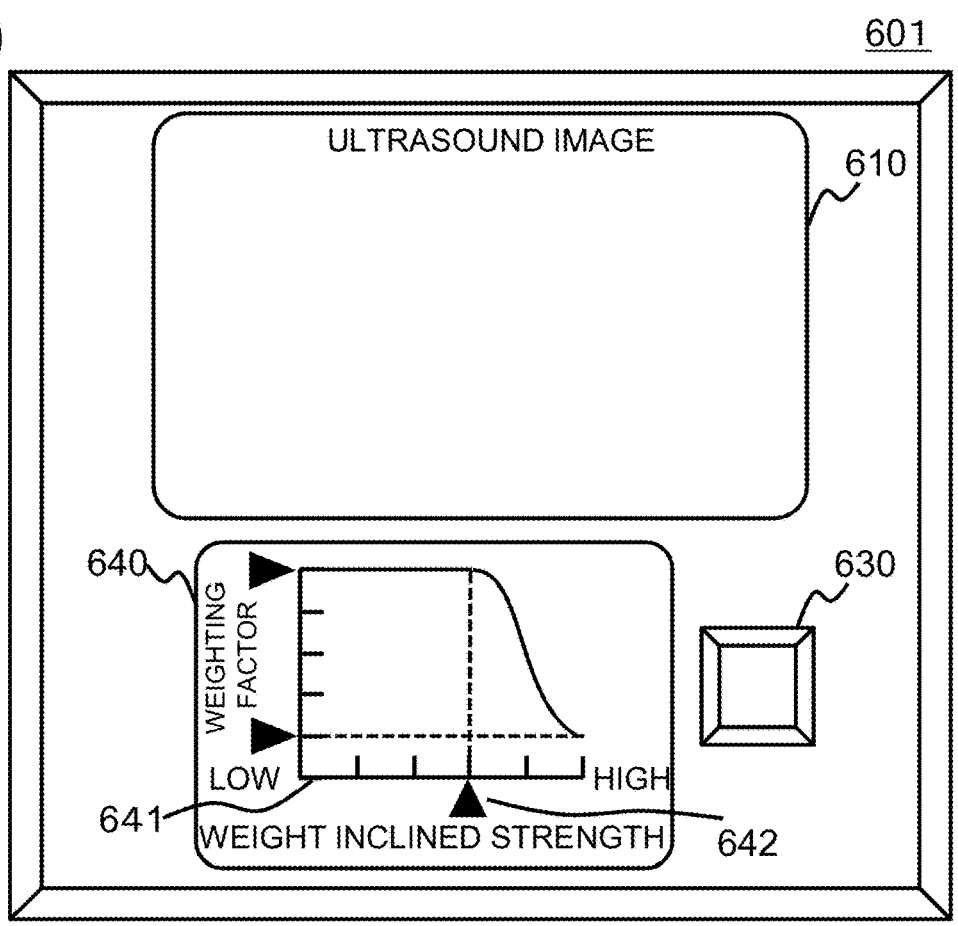

Fig.20
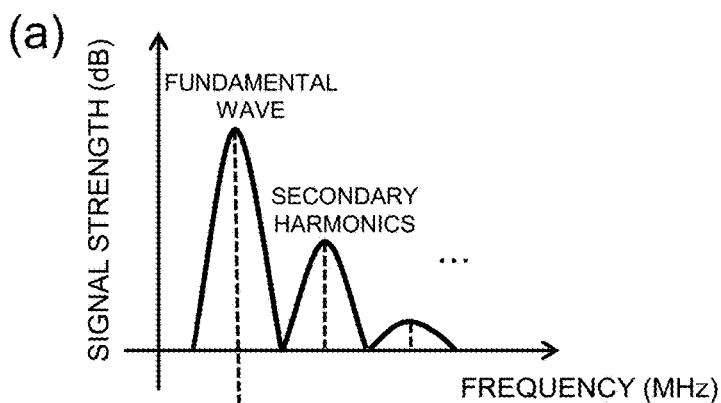
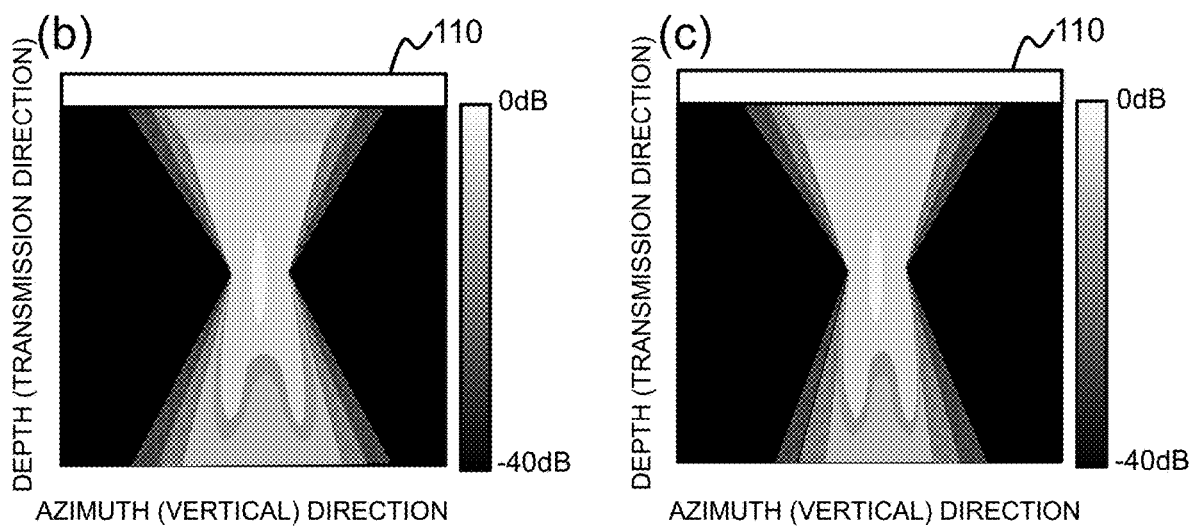

ULTRASONIC IMAGING DEVICE, METHOD FOR ADJUSTING INTER-TRANSMISSION WEIGHT, AND ULTRASONIC IMAGING METHOD

TECHNICAL FIELD

The present invention relates to an ultrasound imaging technique for taking an internal image of a test subject by using ultrasonic waves. In particular, the present invention relates to aperture synthesis techniques for synthesizing phasing signals obtained through multiple transmissions, so as to generate an image from results of the synthesis.

BACKGROUND ART

Medical image display units, notably ultrasound imaging, MRI, and X-ray CT imaging, are widely used as devices for presenting in vivo data incapable of visual check, in the form of numerical values or picture images. In particular, an ultrasound imaging apparatus that is an image display unit using ultrasonic waves, is provided with a higher time resolution relative to other devices, and accordingly it is possible to create an image of pulsating heart without halation, for instance.

The ultrasound imaging apparatus transmits ultrasonic waves into the test subject, receives reflected waves generated in the process of propagation within the test subject, and uses the received signals to create an image of the inside of the test subject. The ultrasound imaging apparatus transmits and receives the ultrasonic waves through multiple ultrasonic elements. Since transmit/receive aperture size is limited, the ends of the element group to be used are influenced by diffraction of the ultrasonic waves, and thus it is difficult to enhance azimuth resolution. In recent years, channel-domain phasing techniques have been studied so as to improve the azimuth resolution, and there have been reported new phasing methods such as adaptive beamformer and aperture synthesis (e.g., see Patent Document 1).

The aperture synthesis is a method to add (to perform inter-transmission synthesis of) phasing signals at an identical point (receive phasing point), obtained by multiple transmissions and receptions, and to obtain signals at respective points in an imaging range. According to the aperture synthesis, it is possible to combine the phasing signals from various directions, obtained through transmissions and receptions via an ultrasound probe, with respect to the receive phasing point. Therefore, it is expected to achieve higher resolution of a point image and robustness against heterogeneity of medium within the test subject. In addition, according to the synthesis process, processing gains are increased, allowing the number of ultrasonic-wave transmissions to be reduced relative to a usual number of times, and thus it is also applicable to high-speed imaging.

PRIOR ART DOCUMENT

Patent Document

Patent Document 1
U.S. Pat. No. 6,685,645 SPECIFICATION

DISCLOSURE OF THE INVENTION

Problems to be Solved by the Invention

In the aperture synthesis, phasing signals at an identical receive phasing point are obtained, through transmissions and receptions at various transmission time points, and the phasing signals corresponding to one frame are added. Through each transmission and reception, there are obtained phasing signals at the receive phasing points within a phasing range that is defined in conformity with transmitted sound waves, and the position of the phasing range within FOV (Field of View) varies time by time. Therefore, the number of additions may vary at every receive phasing point within the imaging range, depending on how the phasing range is defined. Since each phasing signal is amplified in proportion to the addition times, an amplification factor may also vary depending on the addition times. In other words, the amplification factors may become heterogeneous within an image.

If spatial variation of the amplification factor is large, and a difference of the amplification factor, in particular, between adjacent receive phasing points is large, a false image or a luminance distribution different from actuality may be generated, causing image deterioration.

The present invention has been made in view of the situations as described above, and an object of the present invention is to reduce the spatial variation of the amplification factor of the phasing signals at each receive phasing point in the aperture synthesis, and to obtain a high quality image.

Means for Solving the Problems

An ultrasound imaging apparatus of the present invention comprises a receive beamformer for adjusting an inter-transmission weight in accordance with a phasing range, and performing an aperture synthesis, the receive beamformer applying the adjusted inter-transmission weight to phasing signals at the receive phasing points, obtained through transmissions and receptions, and performing inter-transmission synthesis thereon. As to each of the receive phasing points after inter-transmission synthesis is performed, the inter-transmission weight is adjusted in such a manner that a variation form of the amplification factor is smoothed between the adjacent receive phasing points, thereby reducing a difference in the amplification factor.

Advantage of the Invention

According to the present invention, in the aperture synthesis, spatial variation of the amplification factor of the phasing signals with respect to each receive phasing point is reduced, allowing a high quality image to be obtained.

BRIEF DESCRIPTION OF THE DRAWINGS

FIG. 4(a) illustrates an amplification factor of the receive phasing point through one transmission, FIG. 4(b) illustrates a distribution of the amplifier factor when inter-transmission synthesis of all the transmissions for constituting one frame is performed, and FIG. 4(c) is a graph showing variation of the amplification factor on a predetermined receive scanning line;

FIG. 12(a) illustrates the amplification factor of the receive phasing point through one transmission when the inter-transmission weight according to the first embodiment is used, FIG. 12(b) illustrates a distribution of the amplification factor when the inter-transmission synthesis is performed for all the transmissions constituting one frame, with using the same inter-transmission weight; and FIG. 12(c) is a graph showing variation of the amplification factor on a predetermined receive scanning line when the same inter-transmission weight is used;

FIG. 18(a) illustrates an example of parameter acceptance screen according to the third embodiment, and FIG. 18(b) illustrates a modification example of the parameter acceptance screen according to the third embodiment;

FIGS. 20(a) to 20(c) illustrate a modification example of a phasing range decision method.

BEST MODE FOR CARRYING OUT THE INVENTION

First Embodiment

Figure 1:
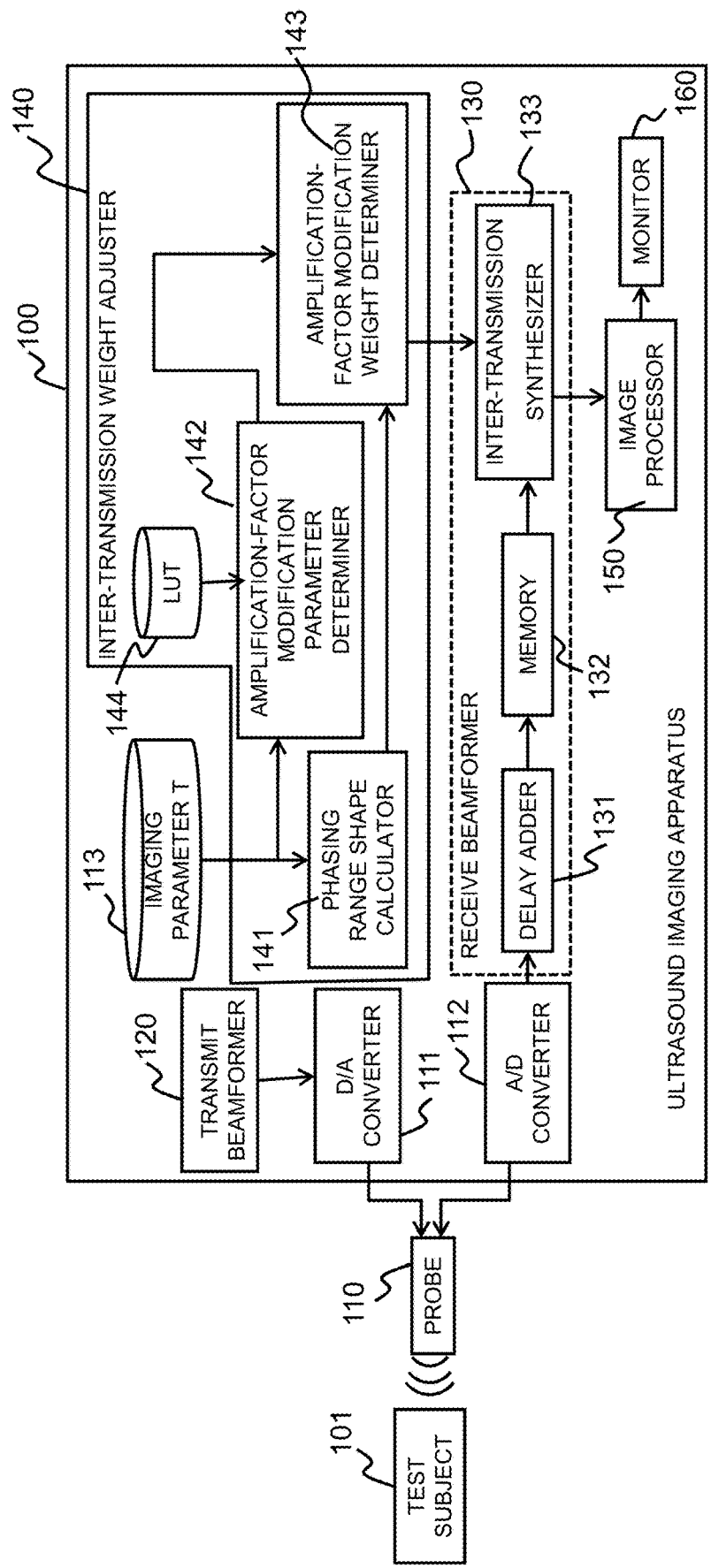
FIG. 1 is a functional block diagram of an ultrasound imaging apparatus according to a first embodiment.

A first embodiment of the present invention will be described with reference to the accompanying drawings. Hereinafter, in all the figures illustrating the embodiment of the present invention, components with an identical function are labeled with the same reference numeral, and they will not be redundantly explained.

[Ultrasound Imaging Apparatus]

An ultrasound imaging apparatus of the present embodiment will now be described. FIG. 1 is a block diagram showing a configuration of the ultrasound imaging apparatus according to the present embodiment. As illustrated, the ultrasound imaging apparatus 100 of the present embodiment is provided with a probe 110, a transmit beamformer 120, a receive beamformer 130, inter-transmission weight adjuster 140, an image processor 150, a monitor 160, a D/A converter 111, an A/D converter 112, and an imaging parameter table (imaging parameter T) 113.

The probe 110 comprises an array of plural ultrasound elements along a predetermined direction. For example, each ultrasound element is a ceramic element, which is made of ceramic. The probe 110 is placed in such a manner that it is brought into contact with a surface of the test subject 101.

The transmit beamformer 120 transmits ultrasonic waves from at least a part of the plural ultrasound elements, via the D/A converter 111. Each of the ultrasonic waves transmitted respectively from the ultrasound elements constituting the probe 110 is provided with a delay time for focusing on a predetermined depth, thereby generating a transmission beam focusing on a predetermined depth.

The D/A converter 111 converts electrical signals of the transmission pulses from the transmit beamformer 120 into acoustic signals. The A/D converter 112 converts the acoustic signals reflected during internal propagation through the test subject 101, received at the probe 110, into electrical signals again, thereby generating received signals.

The receive beamformer 130 receives signals outputted from the ultrasound elements via the A/D converter 112, every transmission, generates phasing signals from thus received signals, and performs aperture synthesis at each point (receive phasing point) within a predetermined phasing range.

The inter-transmission weight adjuster 140 adjusts an inter-transmission weight that is used in the inter-transmission synthesis of the aperture synthesis. The inter-transmission weight is adjusted in accordance with the phasing range. In the present specification, the inter-transmission weight indicates a set of weight values (weighting factors) being applied to respective receive phasing points within the phasing range, thereby controlling strength of the phasing signals at the respective receive phasing points, when the inter-transmission synthesis is performed. The inter-transmission synthesis indicates that, as to the phasing signals at the receive phasing points within the phasing range, being obtained through every transmission and reception performed multiple times, the inter-transmission weight is applied thereto every transmission and reception, and then, the phasing signals after the weight is applied are added with respect to each identical receive phasing point.

The image processor 150 uses the phasing signals after the aperture synthesis is performed to generate an ultrasound image. Then, the monitor 160 displays thus generated ultrasound image.

The imaging parameter table 113 stores various parameters necessary for transmitting and receiving ultrasonic waves, and generating the ultrasound image. The parameters being stored may include, for instance, transmission/reception parameters including a type of the probe 110, a position of the ultrasound element used for transmission, a position on which transmitted sound waves are focused, a transmission beam shape, a position of a receive scanning line, and a sampling frequency of the phasing signal; and parameters for the processing performed in the image processor 150 (image processing parameters).

[Receive Beamformer]

The receive beamformer 130 of the present embodiment performs the aperture synthesis process as described above. As shown in FIG. 1, the receive beamformer 130 is provided with a delay adder 131 configured to delay a received signal obtained by each ultrasound element through one transmission, and then to add the received signals together, thereby phasing the signals to obtain phasing signals as to each receive phasing point, a memory 132 configured to store every transmission, the phasing signals obtained by the delay adder 131 as to each of the receive phasing point, after applying the inter-transmission weight to each of the receive phasing points in the phasing range obtained every transmission and reception, and an inter-transmission synthesizer 133 configured to read from the memory 132, the phasing signals at the receive phasing points obtained every transmission and reception, and to apply the inter-transmission weight being adjusted, respectively to the phasing signals at the receive phasing points, so as to perform the inter-transmission synthesis thereon.

In the present embodiment, the receive beamformer 130 firstly generates the phasing signal according to delay adding processing on the received signal that is received from the A/D converter 112, and further generates a weighted phasing signal obtained by applying the inter-transmission weight to thus generated phasing signal at each receive phasing point. Then, the weighted phasing signals generated through multiple transmissions and receptions are superimposed one on another, and the aperture synthesis is performed on the receive phasing point in a predetermined phasing range. The phasing range indicates a range that includes the receive phasing points used for generating an image, the phasing range being defined in conformity to the transmitted sound waves every transmission and reception. The phasing range may be determined by transmission/reception parameters including the type of the probe 110, the position of the ultrasound element used for transmission, the position on which the transmitted sound waves are focused, and the transmission beam shape.

Figure 2:
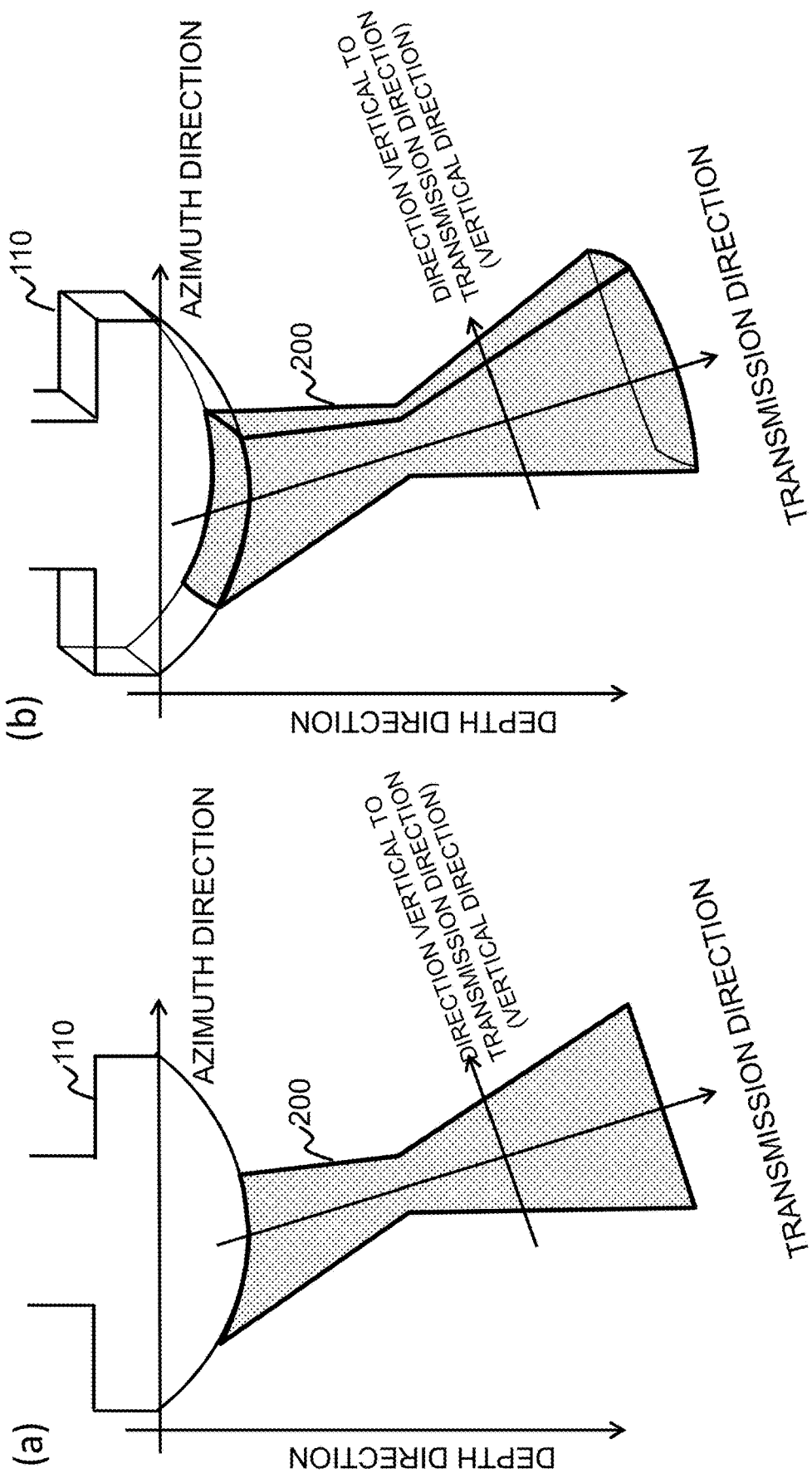
FIG. 2(a) illustrates an example of a phasing range using an 1D probe, when a transmission beam is a focused wave.
FIG. 2(b) illustrates the same phasing range using a 2D probe.

FIG. 2(a) illustrates the phasing range 200 of the 1D probe 110 with an array of one-directional ultrasound elements, in the case where the transmission beam shape is a focused wave. FIG. 2(b) illustrates the phasing range 200 of the 2D probe 110 with a planar arrangement of the ultrasound elements, in the case where the transmission beam shape is the focused wave. In the following, the present embodiment will be described, using such hourglass-shaped model that is obtained by simplifying the phasing range 200 according to the 1D probe 110.

A transmission direction may be defined, for example, as a direction that coincides with a transmission focused point and a bisector of a line segment that connects both ends of the elements used for transmission, or a direction corresponding to a line segment connecting the transmission focused point and the center of the elements used for the transmission. The transmission direction may vary every transmission, similar to the definition of the phasing range 200. By way of example, the phasing range 200 keeps the same shape, if a scanning method of parallel translation is employed for all the transmission times, where the elements used for the transmission and the position of the transmission focused point are subjected to parallel translation. On the other hand, the phasing range 200 may take various shapes every transmission, if another scanning method is employed, where the elements used for the transmission are identical but the transmission focused point is rotated. Further, a direction perpendicular to the transmission direction of the ultrasonic wave will be simply referred to as a vertical direction. In the present specification, an example will now be described, where the transmission direction agrees with a depth direction.

It should be noted that the phasing range 200 is not limited to the shapes as shown in FIGS. 2(a) and 2(b) where the transmission beam is the focused wave. The shape of the transmission beam may be a plane wave or a diffusing wave. In addition, the transmission beam may also be a non-spherical wave where sound propagation distance is not represented by a simple geometric curve or curved surface such as a circular arc and a straight line.

[Delay Adder]

Figure 3:
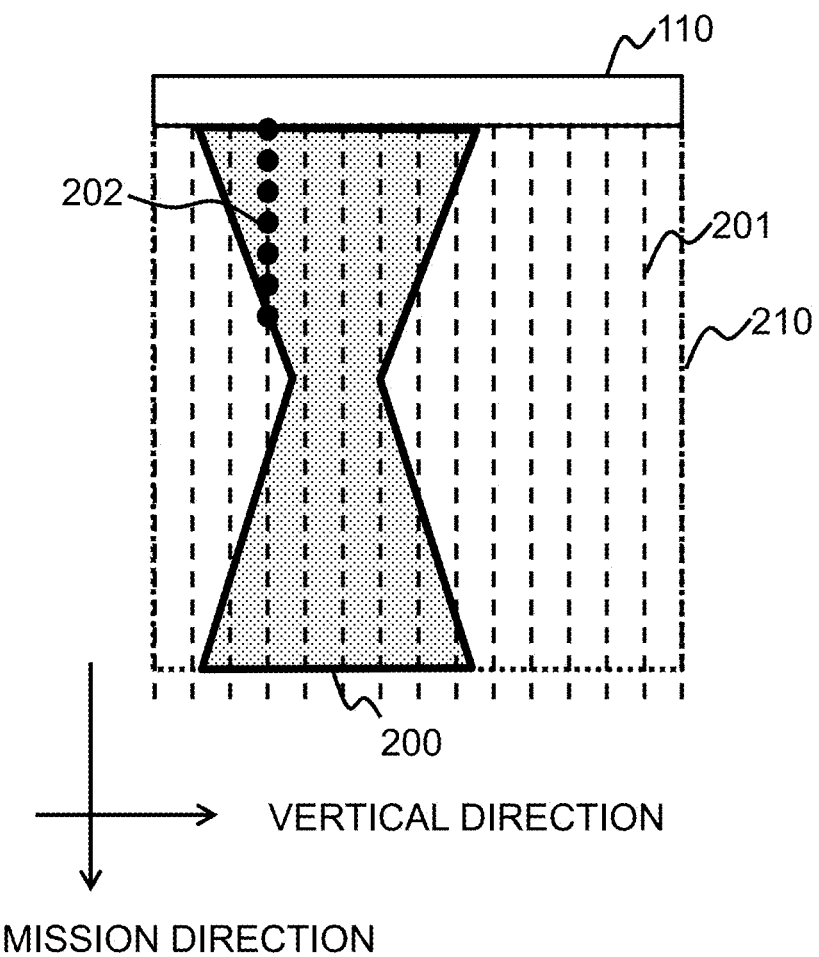
FIG. 3 illustrates the probe, the phasing range, receive scanning lines, and receive phasing points.

The delay adder 131 generates multiple receive beams (receive scanning lines) through parallel processing, from the data received by the ultrasound elements, in response to one-time transmission of ultrasonic waves from the transmit beamformer 120. As shown in FIG. 3, in the present embodiment, the receive scanning line 201 represents a set of the receive phasing points 202, and in general, it indicates a set of multiple receive phasing points 202 on a straight line extending in a predetermined direction. To generate the receive scanning line 201 indicates to generate phasing signals of the respective receive phasing points 202 on the receive scanning line 201. In FIG. 3, the reference numeral 210 denotes an imaging range.

As to each receive phasing point 202, the delay adder 131 delays each of the signals received by the respective ultrasound elements and adds the signals together, so as to obtain the phasing signal of the receive phasing point 202. A delay time given to each received signal is provided for every receive phasing point 202. The delay time may be set to any timing, as far as it is prior to performing the inter-transmission synthesis that utilizes the received signals. By way of example, the delay time may be newly set every transmission, or it may be calculated and set at the time when delay processing is performed for the received signal. Alternatively, it may be preset collectively for a set of all the transmissions and receptions, after configuring imaging mode settings, or the like. In the case of such presetting, the delay time may be held in a table such as an imaging parameter table 113.

In general, the number of the receive scanning lines 201 being formed may be one around the center of the transmission beam, or more lines such as two to eight around the center thereof as in the case of the present embodiment. The number of scanning lines, however, is not limited to those numbers above. By way of example, 32, 64, or 128 receive beams may be generated in parallel.

The receive phasing point 202 is determined according to a type of the probe 110, a position of the ultrasound element in the probe 110 used for transmission, a sampling frequency of the receive scanning line 201, and a range to be imaged (imaging range 210).

[Memory]

The phasing signals obtained by the delay adder 131 as to each receive phasing point 202 are accumulated in the memory 132, with respect to each receive scanning line 201. In other words, the receive scanning lines are generated according to parallel processing every transmission and reception of ultrasonic waves, and a group of phasing signals at respective receive phasing points 202 on each of thus generated receive scanning lines are accumulated in the memory 132.

[Inter-Transmission Synthesizer]

The inter-transmission synthesizer 133 performs inter-transmission synthesis for combining the phasing signals that are obtained through different transmissions and receptions with respect to each receive phasing point 202, among the phasing signals accumulated in the memory 132. In the present embodiment, a weighting factor is specified by an inter-transmission weight adjusted through the inter-transmission weight adjuster 140, and thus specified weighting factor is applied to each receive phasing point 202, so as to add the phasing signals. The phasing signal obtained by the addition is referred to as an inter-transmission composite signal.

[Image Processor and Monitor]

The image processor 150 performs various processing on the inter-transmission composite signals, so as to obtain pixel values corresponding to one frame image. The processing performed on the inter-transmission composite signals may include, for example, detection, compression, interpolation, gray-scaling, and the like. The monitor 160 displays the image obtained by the image processor 150.

[Inter-Transmission Weight Adjuster]

With regard to each receive phasing point 202 after performing the inter-transmission synthesis, the inter-transmission weight adjuster 140 adjusts an inter-transmission weight in such a manner that an amplification-factor difference between adjacent receive phasing points 202 caused by the inter-transmission synthesis, is reduced compared to the case where the inter-transmission weight before the adjustment is applied.

Prior to describing the inter-transmission weight adjuster 140, it will now be described that the inter-transmission synthesis may cause a step-by-step difference in amplification factor, depending on the shape of the phasing range 200.

As described above, among the phasing signals obtained through different transmissions and receptions on identical receive phasing points 202, the inter-transmission synthesizer 133 adds the phasing signals at the receive phasing points 202 within the phasing range 200. As shown in FIG. 4(a), addition of the phasing signals at the receive phasing points 202 within the phasing range 200 is achieved by applying the inter-transmission weight, assuming the weighting factor of the phasing signal as 1 at the receive phasing point 202 within the phasing range 200, and assuming the weighting factor of the phasing signal as 0 at the receive phasing point 202 out of the phasing range 200.

As shown in FIGS. 5(a) to 5(c), even though the shape of the phasing range 200 does not change at any time of transmission and reception, the position within the imaging range 210 varies.

As shown in FIG. 5(d), for the aperture synthesis, the receive phasing points 202 within the phasing ranges 200 are subjected to the inter-transmission synthesis, corresponding to all the transmission times that constitute a frame (e.g., M times, M is an integer 2 or more). In other words, the received signals at the identical receive phasing point 202 are added.

Figure 5:
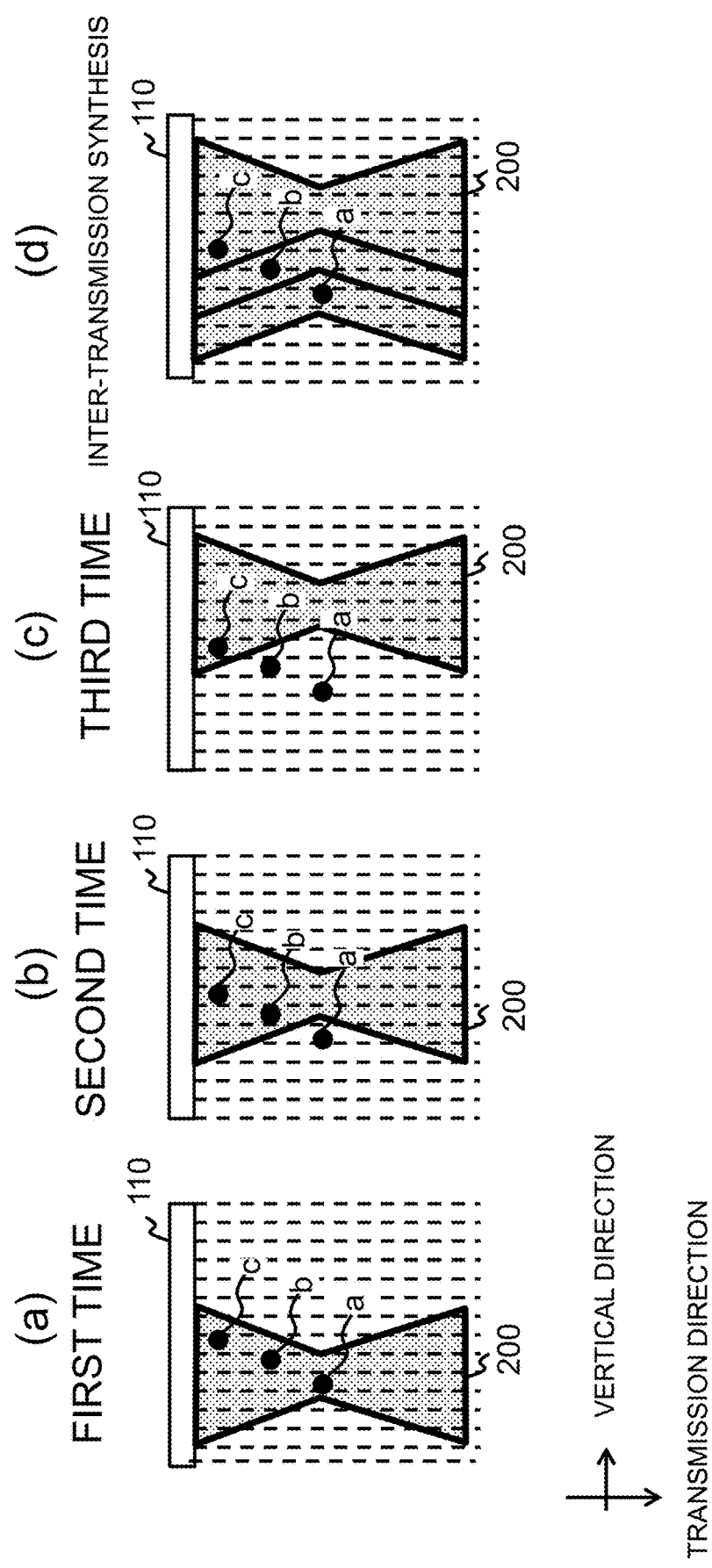
FIGS. 5(a) to 5(d) illustrate why the amplification factor difference occurs in aperture synthesis.

If the phasing range 200 is in the shape as shown in FIG. 5, for example, like the shape with various widths in the direction vertical to the transmission direction, the number of the receive phasing points 202 obtained by one transmission in the vertical direction within the phasing range 200 may be different depending on the position of the transmission direction. Therefore, the number of additions is different depending on the receive phasing point 202.

By way of example as shown in FIGS. 5(a) to 5(d), an example will be described, assuming that the number of transmissions and receptions is three. The receive phasing point "c" is included in the phasing range 200 in each of the first transmission, the second transmission, and the third transmission. Therefore, the number of additions is three. The receive phasing point "b" is included in the phasing range 200 in the first transmission and the second transmission. Therefore, the number of additions is two. On the other hand, the receive phasing point "a" is included in the phasing range 200 only in the first transmission. Therefore, the number of additions is just one.

As for the inter-transmission composite signal, the more is the number of additions, the more intensified is the phasing signal. The number of additions corresponds to an amplification factor, since it indicates how much the phasing signal is amplified.

The amplification factor of the receive phasing point 202 in one transmission is defined as 1, and the amplification factor after the inter-transmission addition is performed N times is defined as N (N is an integer between or equal to 1 and M). In one-frame image, during M-times of transmissions, if the receive phasing point 202 is included in the phasing range 200 in N-times of transmissions and receptions, the receive phasing point 202 is subjected to the addition N times, and the amplification factor of the receive phasing point 202 for this case is N. By way of example, in the aforementioned example as shown in FIG. 5(d), the amplification factor of the receive phasing point "a" is 1, the amplification factor at the point "b" is 2, and the amplification factor at the point "c" is 3.

In general, the inter-transmission weight (the weighting factor 411 at each receive phasing point 202) as shown in FIG. 4(a) is applied, then the inter-transmission synthesis is performed, and FIG. 4(b) shows an inter-transmission synthesis amplification-factor distribution 310 that is obtained by M-times of transmissions. Within this inter-transmission synthesis amplification-factor distribution 310, the amplification factor at each receive phasing point 202 is various within the range from 0 to M.

In this case, as shown in FIG. 4(c), the amplification factors 320 respectively of the receive phasing points 202 on the receive scanning line 311 show discrete variation, taking only integers. Similarly, also in the azimuth direction (vertical direction) that is vertical to the depth direction (transmission direction), the amplification factors shows discrete variation.

In other words, even though the test subject 101 is a medium entirely homogeneous, there may exist discrete variation both in the transmission direction and in the vertical direction, in the inter-transmission composite signals generated through the inter-transmission synthesis. As thus described, if there is a large amplification factor difference in the signal intensity between adjacent receive phasing points 202, a scan conversion process based on the position of the receive scanning line, an interpolation process for generating pixels between the receive scanning lines, a filtering process for noise removal, and the like, may cause brightness variation in the test subject 101, which is not supposed to exist actually. Accordingly, this may deteriorate an image quality.

The present embodiment aims at preventing this kind of significant variation of the amplification factor between the adjacent receive phasing points 202 for the inter-transmission composite signals. In other words, the inter-transmission weight adjuster 140 of the present embodiment adjusts the inter-transmission weight, which is 1 in the phasing range 200, and 0 out of the phasing range 200 as shown in FIG. 4(a), so as to smooth variation of the amplification factor between the adjacent receive phasing points 202. Adjustment of the weighting factor is performed by adjusting a variation form (an inter-transmission weight shape) which corresponds to a set of the weighting factors.

Figure 6:
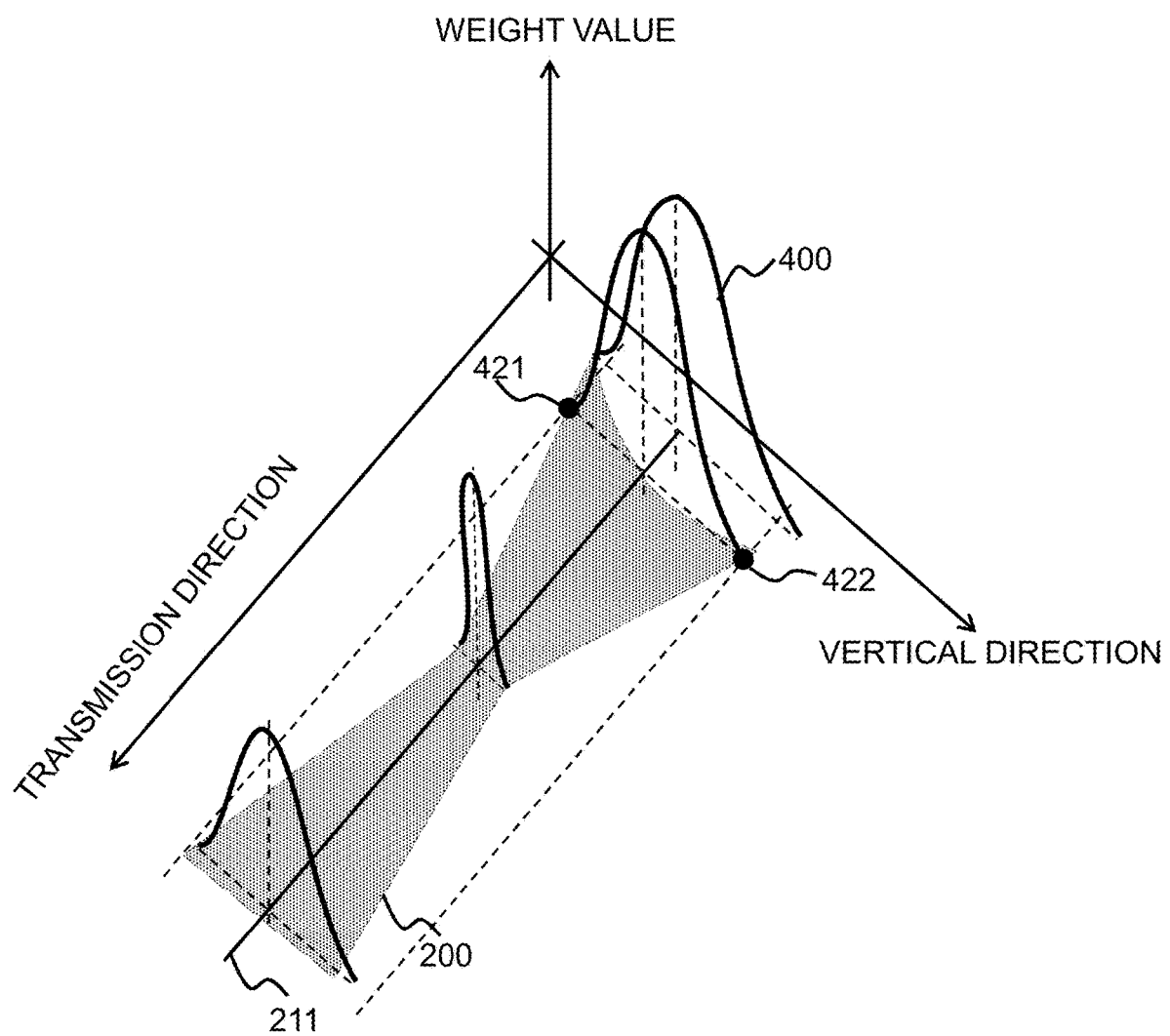
FIG. 6 illustrates the phasing range and inter-transmission weight according to the first embodiment.

As shown in FIG. 6, in the present embodiment, the inter-transmission weight shape 400 is adjusted, for example, in such a manner that a weight value of the receive phasing point 202 on the central receive scanning line 211 is maximized, with respect to the vertical direction of the phasing range, and the value is decreased along with moving away from the center.

In order to adjust the inter-transmission weight shape 400 in this manner, as illustrated in FIG. 1, the inter-transmission weight adjuster 140 of the present embodiment is provided with a phasing range shape calculator 141 configured to calculate a shape of the phasing range 200 every transmission and reception, an amplification-factor modification parameter determiner configured to determine a weight adjustment parameter for specifying the variation form (inter-transmission weight shape) of an adjusted inter-transmission weight within the phasing range 200, an amplification-factor modification weight determiner 143 configured to determine the adjusted inter-transmission weight 400 according to the phasing range 200 and the weight adjustment parameter, and a lookup table LUT 144 configured to hold an optimum weight adjustment parameter in association with an imaging condition.

[Phasing Range Shape Calculator]

The phasing range shape calculator 141 calculates the shape of the phasing range 200. The phasing range 200 is defined on the basis of transmit-receive parameters including a type of the probe 110, a position of the ultrasound element used for transmission, a position on which the transmitted sound waves are focused, and a transmission beam shape. Those information items above are provided in advance by a user as imaging conditions, and held in the imaging parameter table 113. The phasing range shape calculator 141 utilizes those information items acquired from the imaging parameter table 113, so as to calculate the shape of the phasing range 200. In the present embodiment, the position and bounds of the phasing range 200 within the imaging range 210 are specified every transmission and reception.

[Amplification-Factor Modification Parameter Determiner]

As described above, in the present embodiment, the inter-transmission weight shape 400 is adjusted to have the shape where the center in the vertical direction is maximized, monotonously decreasing toward both ends of the phasing range 200. Further as shown in FIG. 6, as to the negative side end 421 and the positive side end 422 in the vertical direction of the phasing range 200 at the same depth in the transmission direction, a distance from the central receive scanning line 211 to the end 421 is not necessarily equal to the distance to the end 422.

Figure 7:
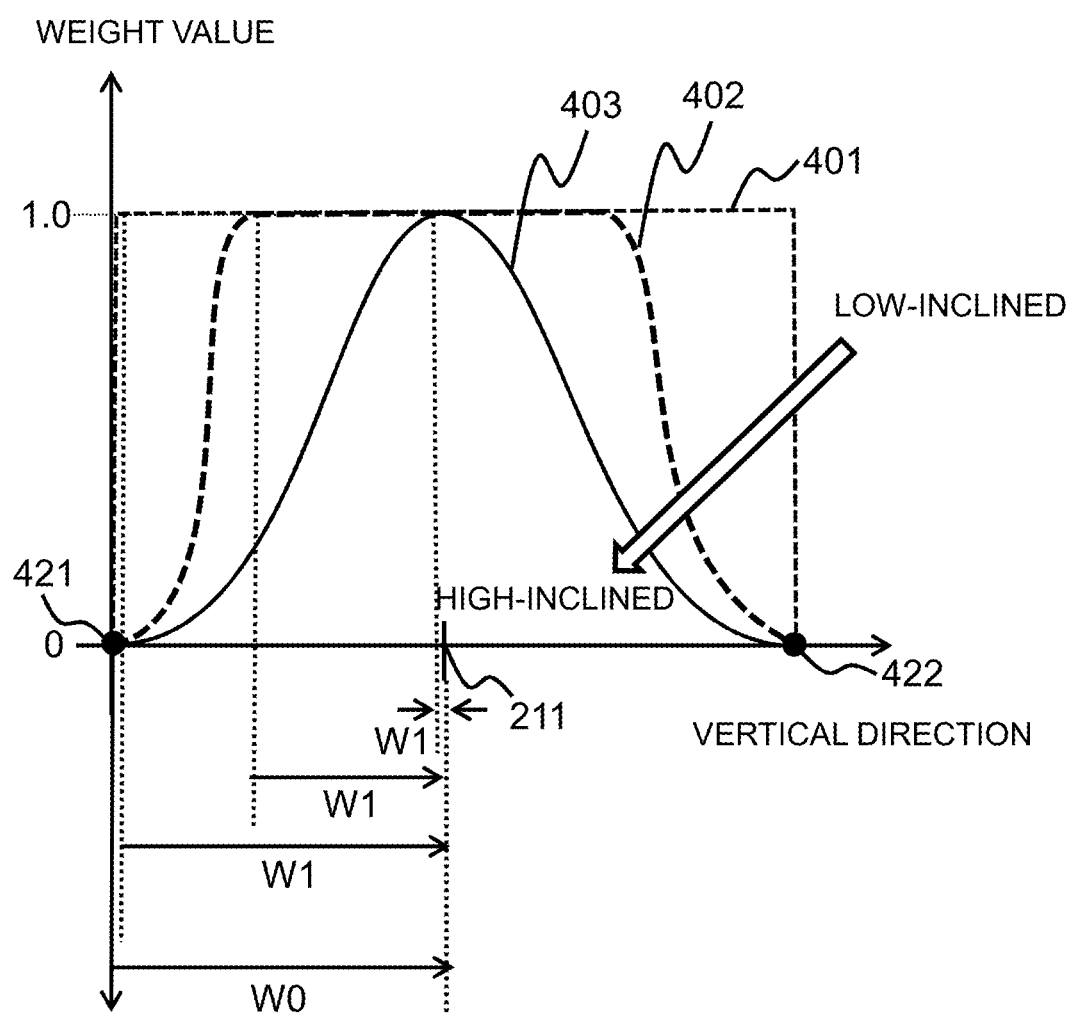
FIG. 7 illustrates a weight adjustment parameter and a shape of the inter-transmission weight variation according to the first embodiment.

As shown in FIG. 7, the inter-transmission weight shape 400 is determined by a function prescribing shape variation, inclined strength, and a minimum value and a maximum value of the weight (weight value width). The function is held in advance by the imaging parameter table 113, or the like, for instance. The weight adjustment parameter determined by the amplification-factor modification parameter determiner 142 of the present embodiment may include inclined strength of a predefined function, and minimum and maximum values of the inter-transmission weight. The function used here may be Hanning function and Gaussian function, for instance.

As shown in FIG. 7, in the present embodiment, as for the inclined strength magnitude, it is defined that the numeral 401 denotes the inter-transmission weight shape with the maximum inclined strength (the strongest), the numeral 403 denotes the inter-transmission weight shape with the minimum inclined strength (the weakest) in the present figure, and the numeral 402 denotes the inter-transmission weight shape with the middle inclined strength therebetween. In other words, the higher is the inclined strength, the steeper becomes the inter-transmission weight shape 400. FIG. 7 is illustrated by plotting the weight values (weighting factors) of the receive phasing points 202 in the vertical direction at a predetermined position of the phasing range 200.

When the inclined strength becomes higher, a degree of manipulating the signal strength by the inter-transmission weight is decreased within the phasing range 200. In other words, with the weighting factor following the inter-transmission weight shape 401, the signal strength at most of the receive phasing points 202 in the phasing range is maintained as it is. On the other hand, in FIG. 7, in the inter-transmission weight shape 403 where the inclined strength is the lowest, the receive phasing points other than the points 202 in proximity to the central received scanning line 211 are multiplied by the weighting factors between or equal to 0 to 1, thereby decreasing the signal strength.

When the inclined strength is high, though a processing-gain improvement effect by the synthesizing process is the largest, variation of the amplification factor may become discrete, and there is a possibility of image quality deterioration. On the other hand, when the inclined strength is made lower, though the processing-gain improvement effect by the synthesizing process may be reduced, variation of the amplification factor becomes smooth and continuous, thereby yielding an effect that the image quality deterioration is prevented.

As described above, effects for preventing the image quality deterioration by the use of the inter-transmission weight are different depending on the inter-transmission weight shape 400. It is desirable to determine the inter-transmission weight shape 400, in such a manner that the shape optimizes the image quality, with consideration of the processing gain as well.

As described above, the weight adjustment parameters include inclined strength, and the minimum/maximum values of the weight. The present embodiment will now be described, taking an example that the minimum weight value is fixed to 0 and the maximum weight value is fixed to 1. In other words, the weight after the adjustment is set to a value within a range from 0 to 1 in the present embodiment.

Therefore, the present embodiment will be described, taking an example that the weight adjustment parameter is only the inclined strength. In other words, in the present embodiment, the amplification-factor modification parameter determiner 142 decides the inclined strength as the weight adjustment parameter.

[LUT]

Figure 8:
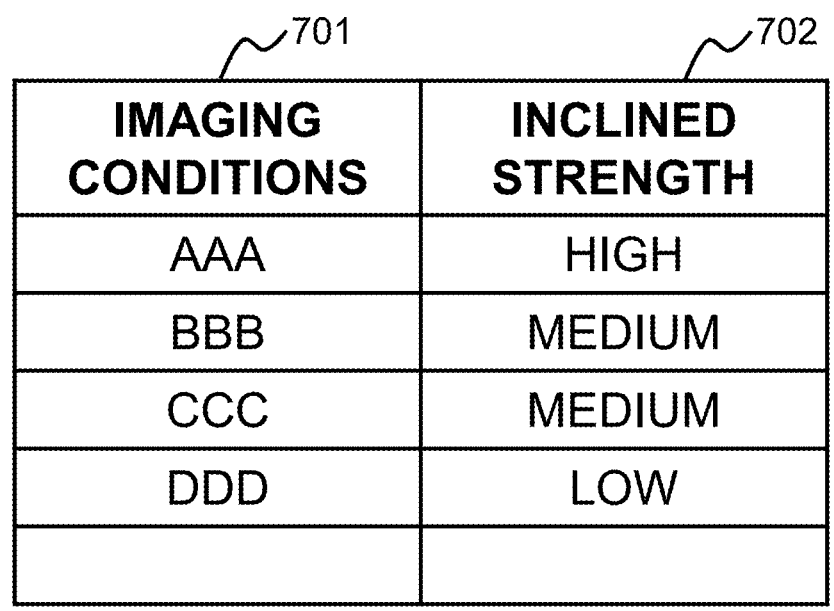
FIG. 8 illustrates an example of a lookup table according to the first embodiment.

The amplification-factor modification parameter determiner 142 of the present embodiment acquires the inclined strength from the LUT 144. FIG. 8 illustrates one example of the LUT 144. As shown in FIG. 8, the LUT 144 holds the weight adjustment parameter values 702 in association with the imaging conditions 701, respectively optimum for the imaging conditions. The imaging conditions 701 to be associated therewith may include, for example, an imaging parameter for specifying the phasing range 200 and a processing parameter used in image processing.

Processing performed in the image processor 150 exerts an influence on the image quality. Therefore, the imaging conditions in the LUT 144 also include parameters for the processing performed in the image processor 150. Processing performed in the image processor 150, influenced by the amplification factor difference (ratio) between adjacent receive phasing points 202, may include a scanning conversion process based on the position of the receive scanning line, an interpolation process for generating pixels between the receive scanning lines, a filtering process for removing noise, and the like. If the ratio of the amplification factor is large, brightness change may occur, even though it does not exist actually in the test subject 101, and accordingly, the image quality may be deteriorated.

The inclined strength 702 may be set in the form of numerical values, or in the form of a strength level which is predefined (e.g., high, medium, and low), for instance. As shown in FIG. 7, the case where numerical values are employed, for example, may use the length W0 from the center of the vertical direction to the end, and the width W1 where the strength keeps the maximum value (here, it is assumed as 1) from the end on the negative side in the vertical direction where the receive phasing point 202 is positioned, thereby employing a value of W1/W0. In addition, if the levels high, medium, and low are employed, for example, they may be associated respectively with the examples 401, 402, and 403 in FIG. 7.

An optimum weight adjustment parameter (inclined strength) is determined in such a manner that a difference (ratio) of the amplification factors between the adjacent receive phasing points 202 does not exceed a permissible range, at each receive phasing point 202 after the inter-transmission synthesis is performed, during the processes performed in the image processor 150 on the subsequent stage.

The amplification factor at each receive phasing point 202 (amplification factor distribution) after the inter-transmission synthesis is performed, is calculated on the basis of the position of the receive scanning line 201, a sampling frequency, the shape of the phase range 200 in every transmission and reception, the position of the phasing range 200 within the imaging range 210, and the weight adjustment parameter. According to this distribution, the amplification factor difference (ratio) between the adjacent receive phasing points 202 is calculated, as to each receive phasing point 202. An acceptable upper limit of the amplification factor difference between the adjacent receive phasing points 202 is assumed to be predetermined, according to restrictions in the processes performed in the image processor 150.

Considering the information as given above, a value of the weight adjustment parameter that does not allow the amplification factor difference between the adjacent receive phasing points 202 to exceed the upper limit according to the processing parameters, is calculated as to each imaging condition, and the calculated weight adjustment parameter values are registered in the LUT 144 in association with the processing parameters and the imaging conditions. In order to improve a depression effect against image deterioration, the weight adjustment parameter is determined in such a manner that the ratio of the amplification factor approaches 1 as possible, for instance.

[Amplification-Factor Modification Weight Determiner]

The amplification-factor modification weight determiner 143 determines an adjusted inter-transmission weight, i.e., a weighting factor by which the phasing signal at each receive phasing point 202 is multiplied, according to the shape of the phasing range 200 calculated by the phasing range shape calculator 141 and the weight adjustment parameter determined by the amplification-factor modification parameter determiner 142.

Figure 9:
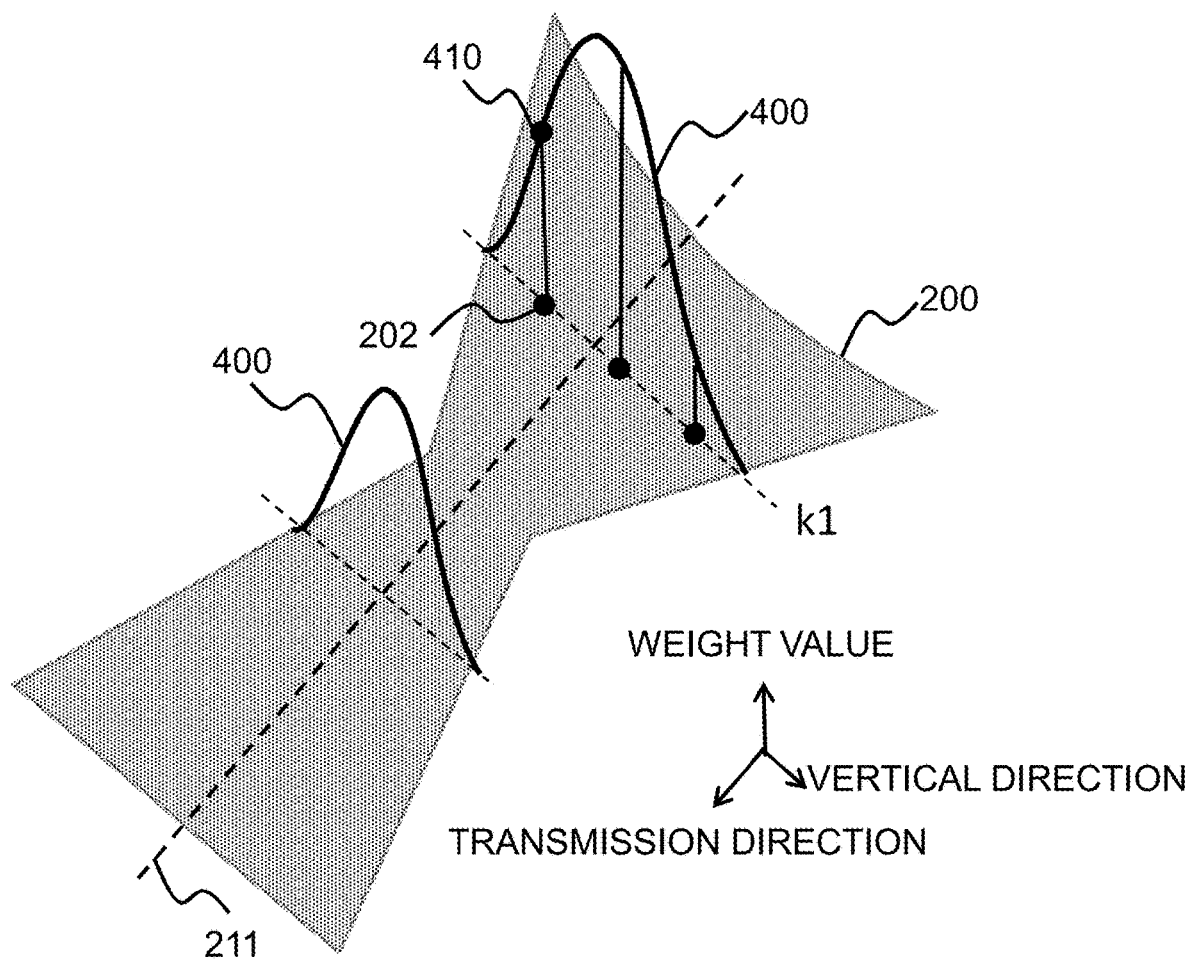
FIG. 9 illustrates a weight decision process performed by an amplification-factor modification weight determiner according to the first embodiment.

As shown in FIG. 9, in the example here, the amplification-factor modification weight determiner 143 specifies the position (k1) of each receive phasing point 202 in the transmission direction. Then, the inter-transmission weight shape 400 at this position (k1) is obtained. The inter-transmission weight shape 400 at the predetermined position in the transmission direction is determined by the width of the phasing range 200 at the position (k1), and the weight adjustment parameter (inclined strength). The width of the phasing range 200 at the position (k1) is calculated from the shape of the phasing range 200. The amplification-factor modification weight determiner 143 calculates a weight value (weighting factor) 410 at each receive phasing point 202 on the position (k1), according to thus determined inter-transmission weight shape 400.

According to the procedures described so far, the amplification-factor modification weight determiner 143 calculates the weighting factors 410 of all the receive phasing points 202 within the phasing range 200 for one-time transmission and reception. Then, the weighting factors 410 of the receive phasing points outside the phasing range 200 are set to 0. This calculation for obtaining the weighting factor 410 is performed every transmission and reception. Thus calculated weighting factors 410 at the respective receive phasing points 202 of the respective transmissions and receptions are transferred to the inter-transmission synthesizer 133, and then they are used for the inter-transmission synthesis.

[Process Flow of Ultrasound Imaging]

Figure 10:
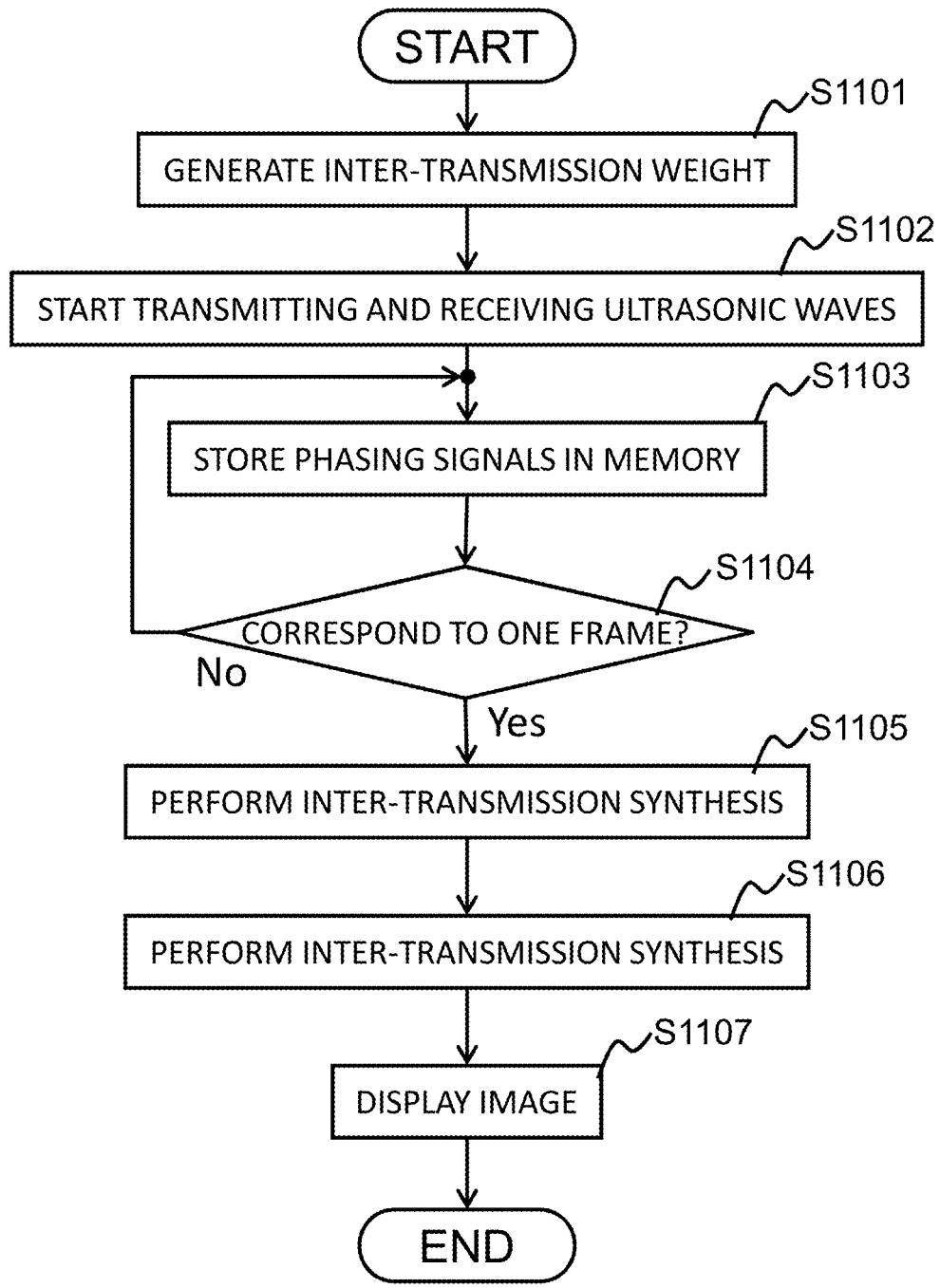
FIG. 10 is a flowchart showing an ultrasound imaging process according to the first embodiment.

Next, a process flow for acquiring an ultrasound image (ultrasound imaging process) of the present embodiment according to each component of the ultrasound imaging apparatus 100 will be described. FIG. 10 shows the process flow of the ultrasound imaging process according to the present embodiment. An operator enters imaging conditions and provides an instruction to start imaging, and then the ultrasound imaging process is started. The process flow will now be described for the case where an image corresponding to one frame is acquired.

Firstly, according to thus provided imaging conditions, the inter-transmission weight adjuster 140 adjusts the inter-transmission weight (step S1101).

The transmit beamformer 120 is activated according to thus provided imaging conditions, and transmission and reception of ultrasonic waves by the probe 110 are started (step S1102). Thereafter, every transmission and reception, the delay adder 131 of the receive beamformer 130 obtains from received signals, phasing signals at the respective receive phasing points 202, and accumulates thus obtained phasing signals in the memory 132 in association with the transmissions and the receive phasing points 202 (step S1103).

When the received signals for one frame are accumulated after repeating transmissions and receptions (step S1104), the inter-transmission synthesizer 133 multiplies the phasing signals of every transmission as to each receive phasing point 202, by the inter-transmission weight adjusted in the step S1101, along with adding those phasing signals, and performs the inter-transmission synthesis (step S1105).

The image processor 150 creates an image from the inter-transmission composite signals generated by the inter-transmission synthesis (step S1106), displays the image on the monitor 160 (step S1107), and completes generation of the ultrasound image for one frame.

The aforementioned process flow has been described under the condition that the inter-transmission weight is generated initially, but this is not the only example. The inter-transmission weight may be generated at any time prior to the step S1105. Specifically, it is generated by using a CPU, an FPGA (Field-Programmable Gate Array), or the like, and held in the memory, or it may be applied to the inter-transmission synthesis without being held in the memory. Alternatively, the inter-transmission weights may be held in advance in the memory 132 or the like, the number of which corresponds to the number of combinations, each being the combination of the transmit-receive parameter and the weight adjustment parameter.

In the example of the process flow described above, every time the phasing signals for one frame are accumulated, multiplication by the inter-transmission weight is performed. It is further possible to configure such that the inter-transmission synthesis in the step S1105 is performed every time phasing signals are acquired by one-time transmission and reception. In this case, every time the phasing signal is obtained, the phasing signal at each receive phasing point 202 is multiplied by the inter-transmission weight, and the result is added to the value already acquired as to the same receive phasing point 202.

[Process Flow of Inter-Transmission Weight Adjustment]

Figure 11:
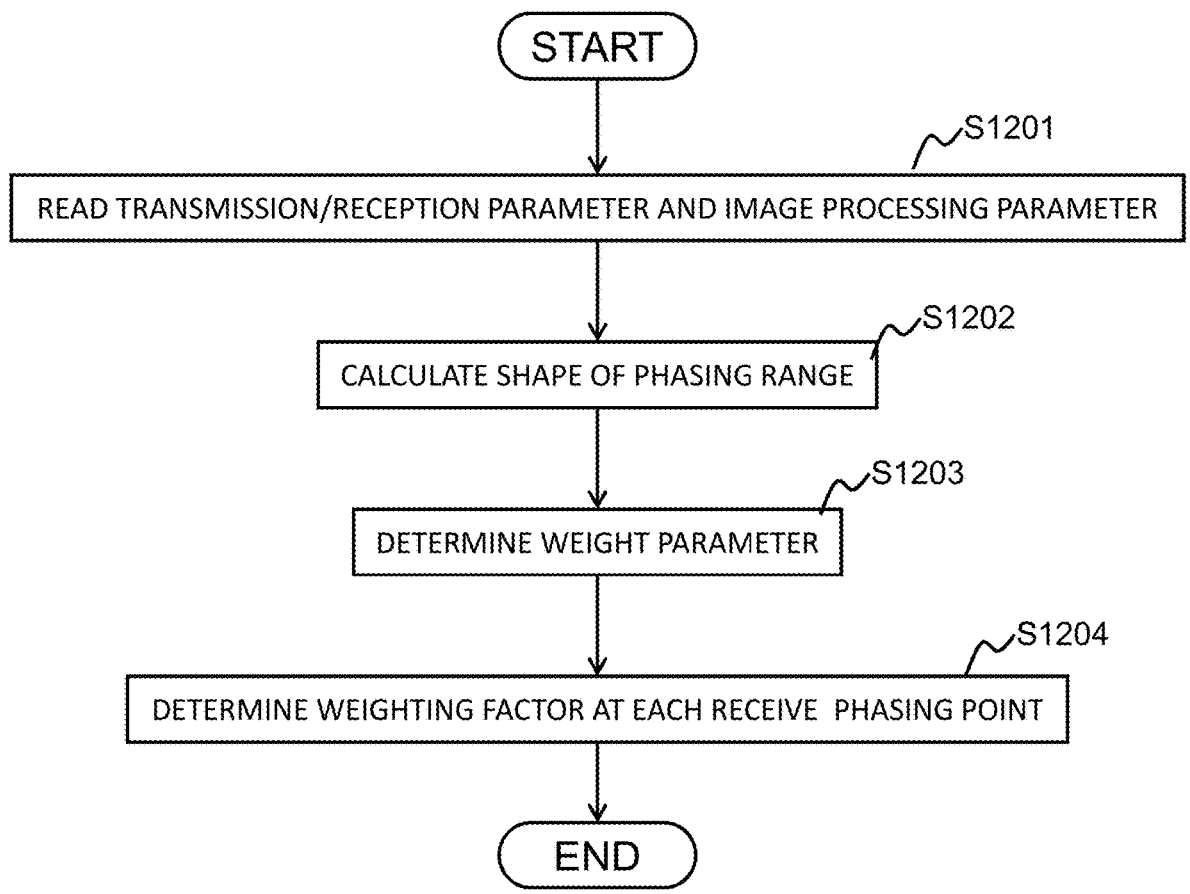
FIG. 11 is a flowchart showing an inter-transmission weight adjusting process according to the first embodiment.
Figure 13:
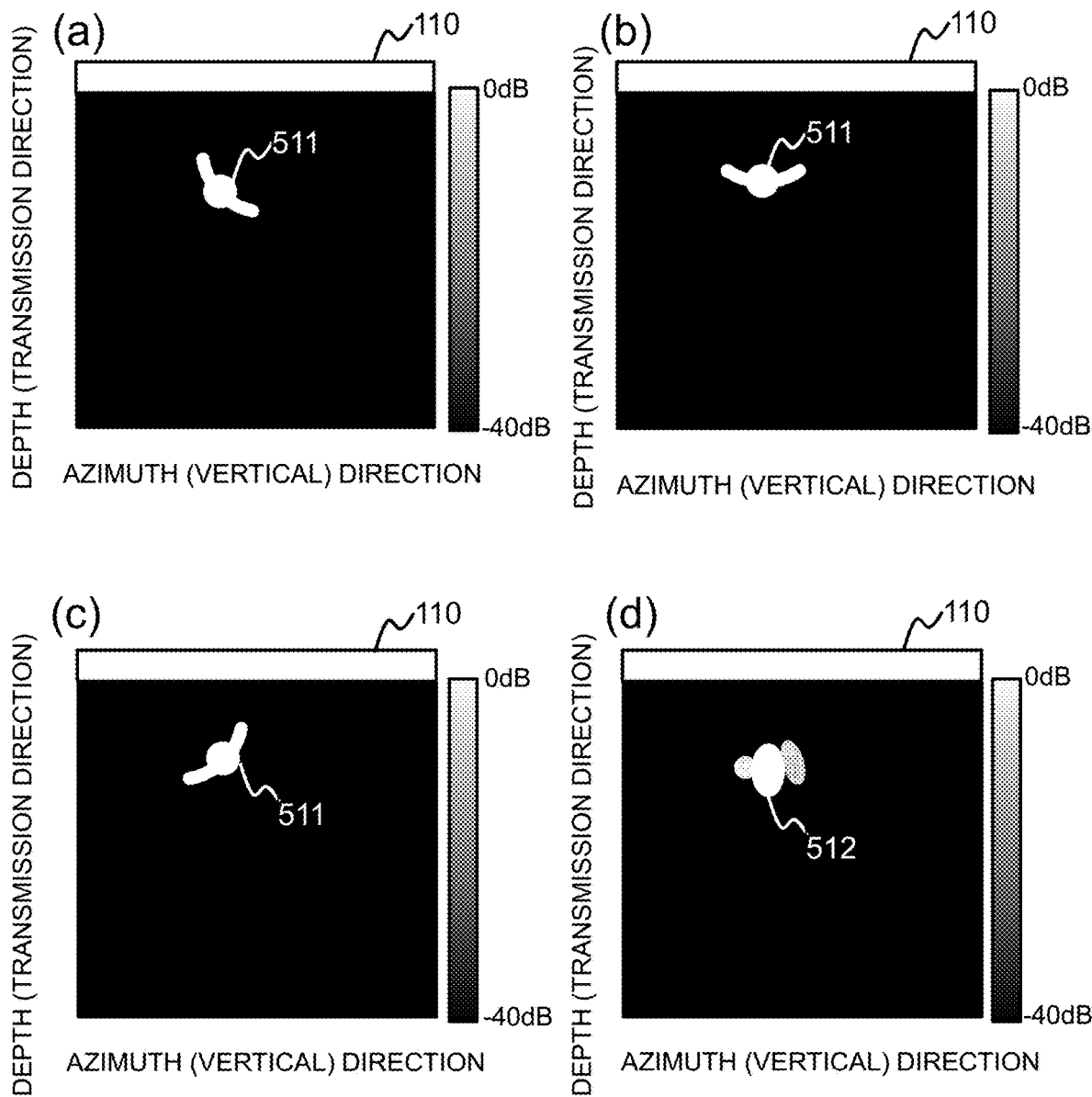
FIGS. 13(a) to 13(c) illustrate the phasing signals respectively obtained through continuous three times transmission and reception, when the inter-transmission weight is not used.
FIG. 13(d) illustrates the phasing signal resulting from the inter-transmission synthesis of the phasing signals shown in FIGS. 13(a) to 13(c)
Figure 14:
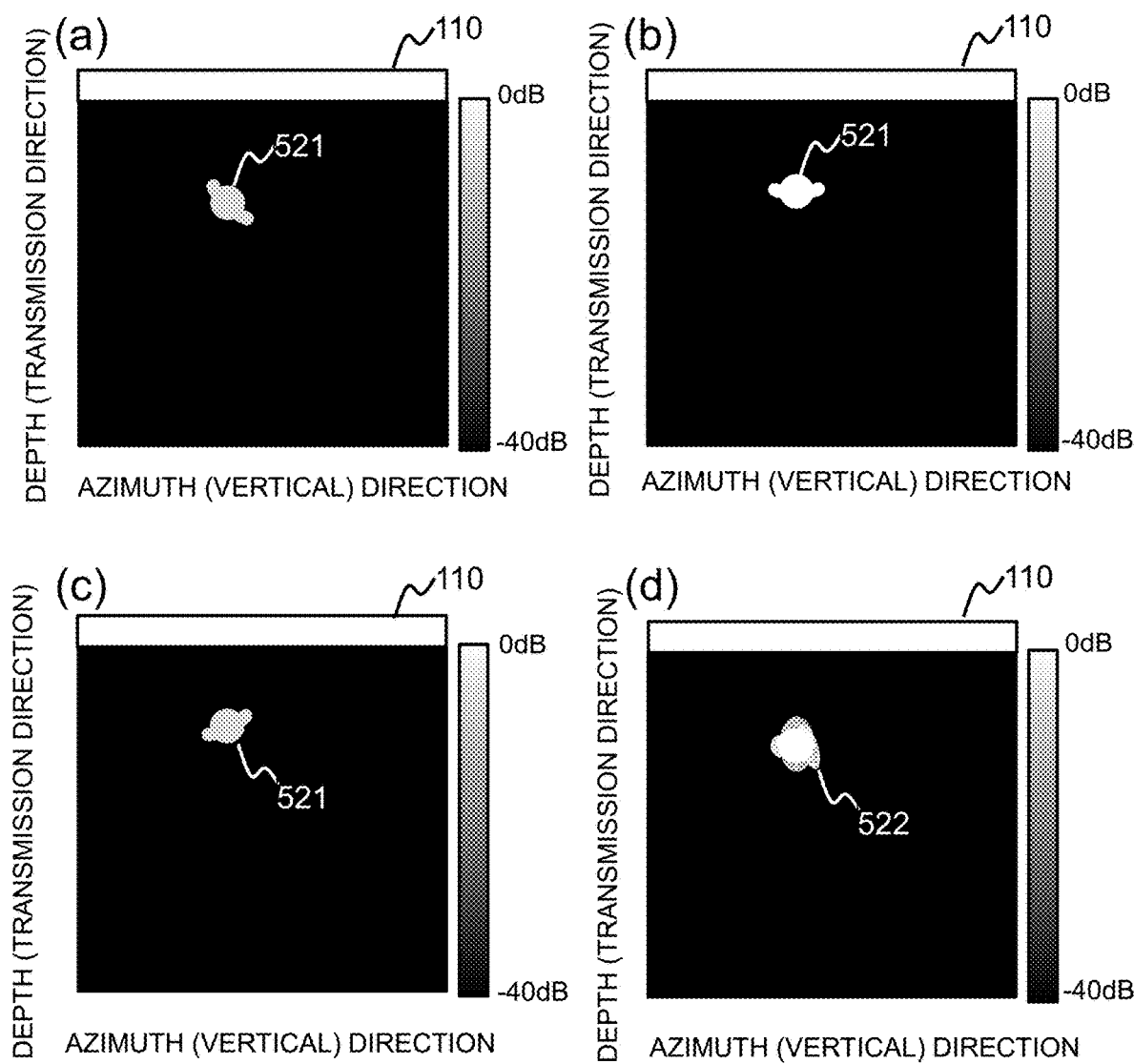
FIGS. 14(a) to 14(c) illustrate the phasing signals respectively obtained through continuous three times transmission and reception, when the inter-transmission weight according to the first embodiment is used.
FIG. 14(d) illustrates the phasing signal resulting from the inter-transmission synthesis of the phasing signals shown in FIGS. 14(a) to 14(c)

Next, a process flow of the inter-transmission weight adjustment of the aforementioned step S1101 according to the inter-transmission weight adjuster 140 will be described. FIG. 11 illustrates the process flow of the inter-transmission weight adjustment according to the present embodiment.

The inter-transmission weight adjuster 140 reads the transmit-receive parameter and processing parameter from the imaging parameter table 113 (step S1201). Then, the phasing range shape calculator 141 uses those parameters to calculate the shape of each of the phasing ranges 200 for all the transmissions constituting one-frame image (step S1202).

The amplification-factor modification parameter determiner 142 acquires from the LUT 144 the weight adjustment parameter which is stored in association with thus read-out imaging conditions (step S1203).

The amplification-factor modification weight determiner 143 determines the weighting factors 410 at the respective receive phasing points 202 within each phasing range 200 of every transmission, according to the shape of the phasing range 200 and the inter-transmission weight shape 400 specified by the weight adjustment parameter, thereby adjusting the inter-transmission weight (step S1204), and the process is completed.

[Simulation Result]

With reference to FIGS. 12(a) to 12(c), there will be described a change of the amplification factor after the inter-transmission synthesis is performed, in the case where the inter-transmission weight 400 of the present embodiment is applied. Here, it is assumed that the phasing range 200 is the same as that of FIG. 4(a).

In the present embodiment, the inter-transmission weight that is equal to 1 within the phasing range 200 and equal to 0 outside the phasing range 200 as shown in FIG. 4(a), is adjusted as shown in FIG. 12(a) in such a manner that the area where the weighting factor 410 around the central axis of the phasing range 200 continues to be 1, and then, it is smoothly shifted to 0 towards both ends of the azimuth direction of the phasing range 200.

A distribution of the amplification factors for one frame after the inter-transmission synthesis is performed is shown in FIG. 12(b), which is obtained by applying the inter-transmission weight as shown in FIG. 12(a) to the receive phasing points 202 within each phasing range 200 and performing the inter-transmission synthesis. The solid line 321 shown in FIG. 12(c) represents the variation of the amplification factor of each receive phasing point 202 on the receive scanning line 311.

As illustrated in those figures, compared to the results as shown in FIGS. 4(b) and 4(c), the distribution of the amplification factor shows more smooth variation, resulting from the application of the inter-transmission weight and the inter-transmission synthesis according to the present embodiment.

In the present embodiment as described above, the transmission weight shape 400 at each position in the depth direction (transmission direction) is determined in accordance with the width of the phasing range 200 at the position. Therefore, as indicated by the solid line 321 in FIG. 12(c), the amplification factor of each of the receive phasing points 202 on the receive scanning line 311 may take a value of decimals, thereby rendering the variation smooth and continuous. It is to be noted that the dotted line 320 indicates the amplification factor that is shown in FIG. 4(c).

In addition, the inter-transmission weight shape 400 in the vertical direction has the shape showing the maximum value at the center and decreasing as approaching to the ends. Accordingly, also in the vertical direction (azimuth direction), the variation of the amplification factor of the present embodiment becomes smooth and continuous.

As described above, the ultrasound imaging apparatus of the present embodiment is provided with the probe 110 having an array of multiple ultrasound elements along the predetermined directions, the transmit beamformer 120 configured to transmit ultrasonic waves from at least a part of the multiple ultrasound elements, the receive beamformer 130 configured to generate phasing signals from the received signals outputted from the ultrasound elements, and to perform aperture synthesis on the receive phasing points 202 within the predetermined phasing range 200, the inter-transmission weight adjuster 140 configured to adjust the inter-transmission weight used in the inter-transmission synthesis for the aperture synthesis, and the image processor 150 configured to generate an ultrasound image from the phasing signals after the aperture synthesis is performed, wherein, the transmit beamformer 120 gives a delay time to each of the ultrasound waves transmitted from the respective ultrasound elements, so as to focus the ultrasound waves to a predetermined depth, and the receive beamformer 130 is provided with the delay adder 131 configured to delay each of the received signals obtained by the ultrasound elements in one-time transmission, and then add those delayed signals, so as to perform phasing and to obtain phasing signals, and the inter-transmission synthesizer 133 configured to apply the adjusted inter-transmission weight to each of the phasing signals at the receive phasing point 202, obtained every transmission and reception, and to perform the inter-transmission synthesis, and the inter-transmission weight adjuster 140 configured to adjust the inter-transmission weight in accordance with the phasing range 200.

In this case, the inter-transmission weight adjuster 140 may adjust the inter-transmission weight, as to each receive phasing point 202 after the inter-transmission synthesis is performed, so that the amplification factor difference between the adjacent receive phasing points 202 is reduced. The inter-transmission weight adjuster 140 may further be provided with the phasing range shape calculator 141 configured to calculate the shape of the phasing range 200 every transmission and reception, the amplification-factor modification parameter determiner 142 configured to determine the weight adjustment parameter for specifying the variation form (inter-transmission weight shape 400) of the adjusted inter-transmission weight value within the phasing range 200, and the amplification-factor modification weight determiner 143 configured to determine the adjusted inter-transmission weight according to the phasing range 200 and the weight adjustment parameter. Then, the inter-transmission weight adjuster 140 may further be provided with the lookup table 144 for holding the weight adjustment parameter values in association with the imaging conditions, and the amplification-factor modification parameter determiner 142 may acquire the weight adjustment parameter from the lookup table 144.

As described above, according to the present embodiment, the receive phasing point 202 obtained every transmission and reception is multiplied by the inter-transmission weight that is adjusted in accordance with the phasing range 200, and the inter-transmission synthesis is performed. Therefore, in the inter-transmission composite signals obtained by the inter-transmission synthesis, variation of the amplification factor (amplification factor difference) between the adjacent receive phasing points 202 becomes smaller, and the variation of the amplification factor becomes smoother in both the transmission direction and the vertical direction.

In other words, by using the adjusted inter-transmission weight of the present embodiment, it is possible to reduce a false image and/or image deterioration such as a brightness distribution different from the actuals, which are generated by a large amplification factor difference in signal strength between the adjacent receive phasing points 202, caused by the aperture synthesis. Accordingly, precision enhancement in diagnosis and reduction of examination time can be expected.

Furthermore, in the present embodiment, there is employed a distribution shape as the inter-transmission weight shape 400, which is the maximum at the central axis (central receive scanning line 211) (center) of the phasing range 200 in the vertical direction (azimuth direction), and becomes smaller towards both ends of the phasing range 200. Therefore, it is possible to increase a degree of contribution to the phasing signals at the receive phasing points 202 around the center of the phasing range where the signal reliability is high, and to decrease the degree of contribution to the phasing signals around the ends of the phasing range where the signal reliability is low.

By way of example, even though the phasing range 200 has the shape with the same width at every position in the transmission direction, the signal reliability around the ends in the vertical direction is lower than the signal reliability around the center. In this case, by using the adjusted inter-transmission weight of the present embodiment, a degree of contribution of the signals with high reliability can be increased, with reducing the contribution of the signals with low reliability, thereby obtaining a higher quality image.

In addition, the contribution of the phasing signals with low reliability around both ends is reduced, thereby yielding an effect to prevent artifacts that are likely to be generated within an image of one frame, in the case where the imaging target is in motion during the imaging.

With reference to FIGS. 13(a) to 14(d), this effect will be described. By way of example, there is considered a situation that one-point reflector is imaged, which moves from a deep portion to a shallow portion in the depth direction.

FIGS. 13(a) to 13(c) illustrate visualized phasing signals, obtained respectively in consecutive three transmissions. The shape of the point image 511 obtained in each of the transmissions depends mainly on the type of the probe 110, the position of the element used for the transmission, and the position of the transmission focused point.

FIG. 13(d) illustrates a result 512 according to a conventional method, that is, an inter-transmission weight before adjustment was applied and the phasing signals of the respective transmissions were subjected to the inter-transmission synthesis. In this case, as illustrated, two types of artifacts were produced. The first artifact was caused by extension of the point image in the depth direction due to the movement of the point image 511 from the deep portion to the shallow portion. The second artifact occurred in the azimuth direction, which was caused by the signals mutually intensified at a position where the point image 511 did not exist actually, as a result of superimposing one shape of the point image 511 on another in the respective transmissions.

In the present embodiment, the inter-transmission weight is used, which follows the inter-transmission weight shape 400 that is adjusted in such a manner that the weight value is smoothly decreased from the central axis of the phasing range 200 to the ends in the azimuth direction, thereby reducing the signal strength of the phasing signal obtained in one transmission. FIGS. 14(a) to 14(c) illustrate that the adjusted inter-transmission weight of the present embodiment was applied to the group of signals as shown in FIGS. 13(a) to 13(c). In those figures, the reference numeral 521 indicates the point image.

As illustrated in those figures, by applying the adjusted inter-transmission weight of the present embodiment, signal strength of the phasing signal obtained in one transmission was adjusted, position by position. FIG. 14(d) illustrates the result of inter-transmission synthesis of those signals. As illustrated in those figures, the signal to which the adjusted inter-transmission weight of the present embodiment was applied and subjected to the inter-transmission synthesis, showed less artifacts on the point image 522 in the depth direction and in the azimuth direction, compared to the signal according to the conventional method as shown in FIG. 13(d).

Second Embodiment

Next, the second embodiment of the present invention will be described. In the first embodiment, for adjusting the inter-transmission weight, the weight adjustment parameter (inclined strength) is acquired from the LUT that is prepared in advance. On the other hand, in the present embodiment, instead of preparing the LUT, and an appropriate weight adjustment parameter is determined according to a search.

Figure 15:
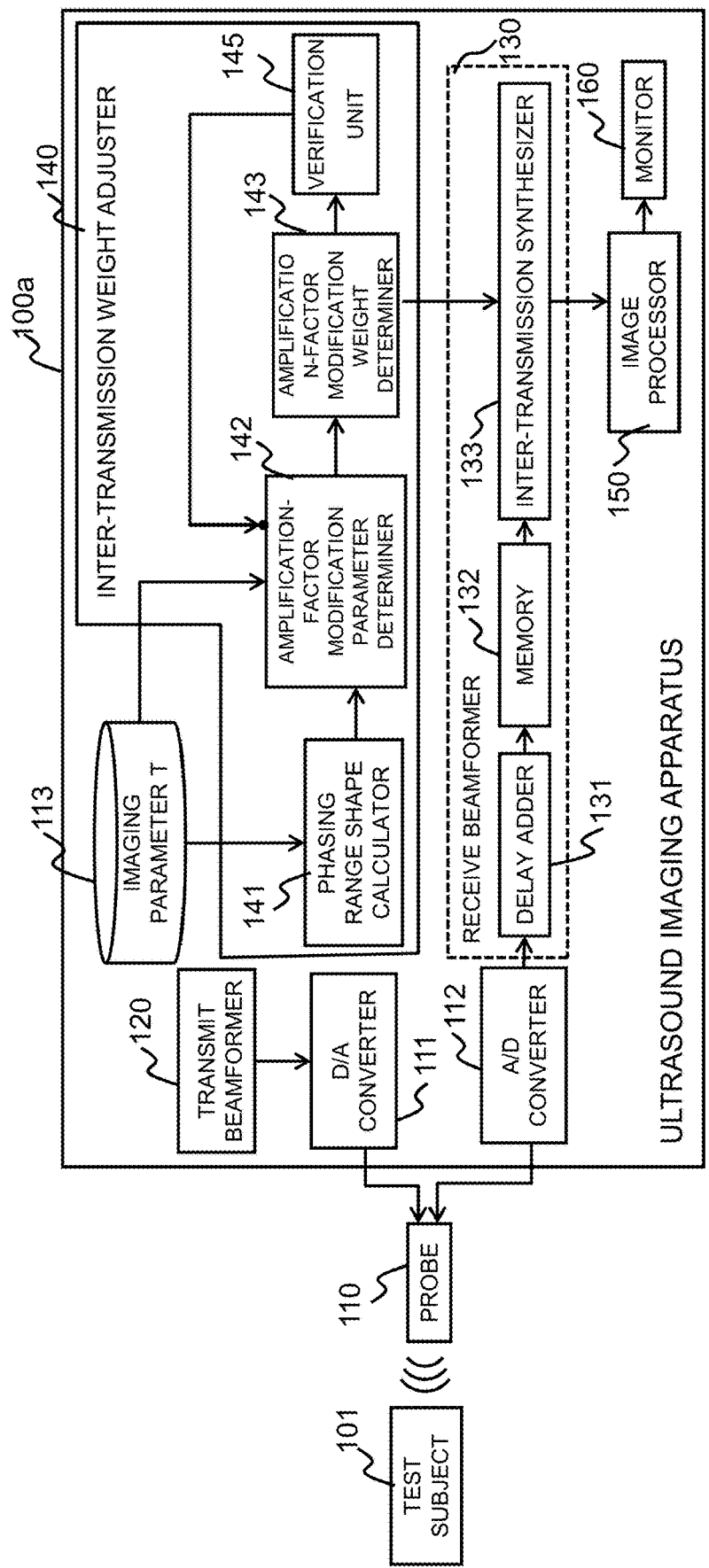
FIG. 15 is a functional block diagram of the ultrasound imaging apparatus according to a second embodiment.

FIG. 15 is a functional block diagram showing the ultrasound imaging apparatus 100a of the present embodiment. As illustrated, the ultrasound imaging apparatus 100a of the present embodiment has basically the same configuration as the first embodiment. However, since a method of determining the weight adjustment parameter is different, the inter-transmission weight adjuster 140 is not provided with the LUT 144. Instead, the inter-transmission weight adjuster 140 is provided with a verification unit 145 configured to verify suitability of the inter-transmission weight that is determined by the amplification-factor modification weight determiner 143. In addition, processing of the amplification-factor modification parameter determiner 142 is also different.

The present embodiment will now be described, focusing on the configuration that is different from the first embodiment.

[Amplification-Factor Modification Parameter Determiner]

The amplification-factor modification parameter determiner 142 of the present embodiment determines the weight adjustment parameter that specifies the adjusted inter-transmission weight shape 400, in accordance with the shape of the phasing range 200, similar to the first embodiment. Since the LUT 144 is not provided in the present embodiment, a predefined initial value Winc0 is set as inclined strength that is the weight adjustment parameter to be determined. Then, when the verification unit 145 determines the parameter as inappropriate, the amplification-factor modification parameter determiner 142 varies the value of the weight adjustment parameter, by a predefined amount of change ΔWinc, thereby determining an optimum weight adjustment parameter.

By way of example, the amplification-factor modification parameter determiner 142 sets a conceivably largest inclined strength as the initial value Winc0, using a predefined fixed value as the amount of change ΔWinc, and renders the inclination to be more gentle gradually to an optimum value. The initial value Winc0 and the amount of change Winc may be held in advance in the imaging parameter table 113, or the like, for instance.

[Verification Unit]

The verification unit 145 of the present embodiment verifies suitability of the adjusted inter-transmission weight. In the present embodiment, the suitability is determined according to a result of the inter-transmission synthesis of the inter-transmission weights.

Specifically, weighting factors 410 are obtained, on the respective receive phasing points 202 every transmission, which are determined by the amplification-factor modification weight determiner 143, according to the weight adjustment parameter that is provided every transmission by the amplification-factor modification parameter determiner 142. Then, only the weighting factors 410 are subjected to the inter-transmission synthesis. In other words, as to an identical receive phasing point 202, the weighting factors 410 of the receive phasing point 202 in every transmission and reception are added.

Then, the verification unit 145 determines as inappropriate, the result of the inter-transmission synthesis that is performed on the adjusted inter-transmission weights every transmission and reception, when a maximum value of the ratio of the weight values between the adjacent receive phasing points 200 is larger than a predetermined threshold. It should be noted that the threshold may be defined in advance, and it may be stored in the imaging parameter table 113, or the like, for instance.

[Process Flow of Inter-Transmission Weight Adjustment]

Figure 16:
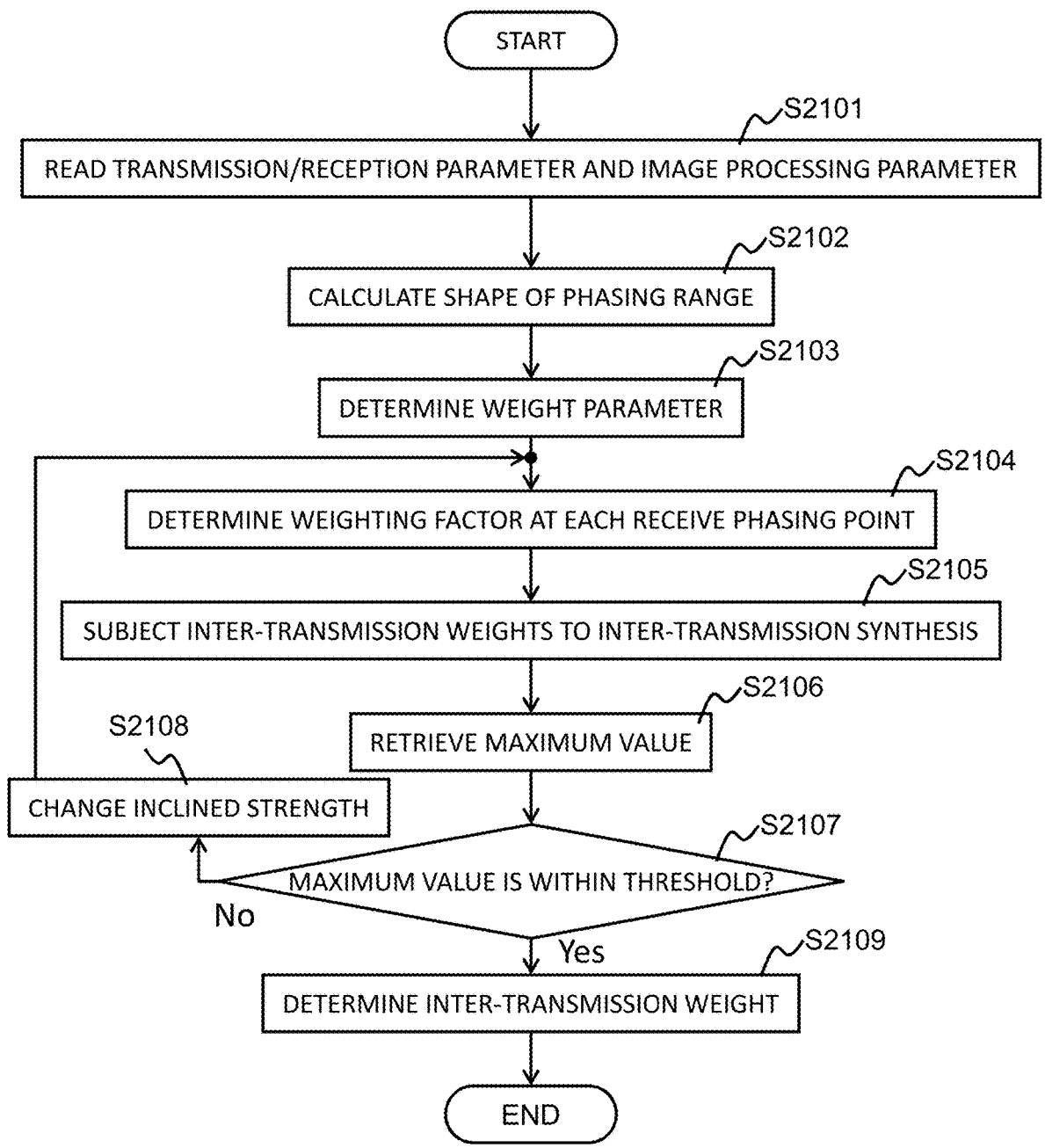
FIG. 16 is a flowchart showing the inter-transmission weight adjusting process according to the second embodiment.

With reference to FIG. 16, there will now be described an inter-transmission weight adjusting process flow according to the inter-transmission weight adjuster 140 of the present embodiment.

The phasing range shape calculator 141 reads the transmit-receive parameter and the image processing parameter from the imaging parameter table 113 (step S2101). Then, the phasing range shape calculator 141 utilizes those parameters, so as to calculate each shape of the phasing ranges 200 corresponding to all the transmissions, which constitute one frame image (step S2102).

The amplification-factor modification parameter determiner 142 reads an initial value of the weight adjustment parameter from the imaging parameter table 113, and determines this value as the weight adjustment parameter (step S2103).

The amplification-factor modification weight determiner 143 determines the weighting factor 410 of the receive phasing point 202 within each phasing range 200 of every transmission, according to the shape of the phasing range 200 calculated in the step S2102, and the inter-transmission weight shape 400 specified by the weight adjustment parameter (step S2104).

The verification unit 145 subjects the inter-transmission weights (a set of the weighting factors 410 of each receive phasing point 202) of every transmission, to the inter-transmission synthesis (step S2105), and generates an amplification factor distribution. In this example, as described above, the weighting factors 410 are added as to an identical receive phasing point 202, and generates the amplification factor distribution.

The verification unit 145 makes comparison between the ratios of the amplification factors of adjacent receive phasing points 202 in the amplification factor distribution, and the highest value is extracted (step S2106). Then, thus extracted value is compared with a threshold which is a predetermined amplification factor ratio (step S2107).

When the extracted maximum value of the amplification factor ratio exceeds the threshold, the amplification-factor modification parameter determiner 142 is notified that thus generated weight adjustment parameter is inappropriate. Upon receipt of this notification, the amplification-factor modification parameter determiner 142 changes the weight adjustment parameter (inclined strength) according to the aforementioned method (step S2108), proceeds with the step S2104, and repeats the processing.

On the other hand, when the maximum value is equal to or less than the threshold, the verification unit 145 notifies the amplification-factor modification weight determiner 143 that the adjusted inter-transmission weight is appropriate, and the inter-transmission weight adjuster 140 determines the inter-transmission weight thus adjusted at the point of time, as the adjusted inter-transmission weight (step S2109), and completes the process.

Similar to the first embodiment, the inter-transmission synthesizer 133 of the present embodiment utilizes the inter-transmission weights (a set of weighting factors 410 on the respective receive phasing points 202) adjusted by the inter-transmission weight adjuster 140, so as to perform the inter-transmission synthesis for aperture synthesis. Then, the image processor 150 generates an image from a result of the aperture synthesis, and displays the image on the monitor 160.

As described above, the ultrasound imaging apparatus 100a of the present embodiment is provided with, similar to the first embodiment, the probe 110, the transmit beamformer 120, the receive beamformer 130, the inter-transmission weight adjuster 140, and the image processor 150. The inter-transmission weight adjuster 140 may adjust the inter-transmission weight in such a manner that an amplification factor difference between the adjacent receive phasing points 202 is reduced, as to each receive phasing point 202 after the inter-transmission synthesis is performed. In addition, the inter-transmission weight adjuster 140 may be provided with the phasing range shape calculator 141, the amplification-factor modification parameter determiner 142, and the amplification-factor modification weight determiner 143.

The inter-transmission weight adjuster 140 is further provided with the verification unit 145 configured to verify the suitability of the inter-transmission weight determined by the amplification-factor modification weight determiner 143, and when it is determined that the inter-transmission weight is inappropriate, the amplification-factor modification parameter determiner 142 may change the value of the weight adjustment parameter, by a predetermined amount.

As described above, according to the present embodiment, similar to the first embodiment, it is possible to obtain smooth variation of the amplification factors of the receive phasing points 202 in the image after the inter-transmission synthesis is performed. Since the image is generated from a group of the phasing signals to which the inter-transmission weights are applied as described above, an image with less artifacts can be obtained.

Further according to the present embodiment, since there is no LUT, a memory area prepared for the LUT becomes unnecessary. Therefore, a high-quality image can be obtained even with a simpler configuration.

In the embodiments as described so far, optimum inclined strength is determined by gradually reducing the inclined strength from the initial value Winc0 which is the maximum value. However, this method is not the only searching method for the optimum inclined strength.

By way of example, searching for the optimum value may be made by a half-split approach, starting from a maximum value, a minimum value, or a medium value.

Further, also in the present embodiment, similar to the first embodiment, the LUT 144 may be provided for holding optimum weight adjustment parameter values respectively in association with imaging conditions. By way of example, if the LUT 144 does not hold data which is associated with the imaging conditions provided at the imaging time, the weight adjustment parameter values held in association with the nearest imaging conditions are retrieved from the LUT 144, and then, they are optimized by searching.

Third Embodiment

A third embodiment of the present invention will now be described. In the present embodiment, the image is displayed, which is obtained from the result of the aperture synthesis by using the adjusted inter-transmission weight, and further adjustment of the weight adjustment parameter is accepted from a user.

An initial inter-transmission weight may be calculated according to any of the following methods, the method of the first embodiment or the method of the second embodiment. Alternatively, the method may be determined in advance. In the following, the case where calculation is made according to the method of the first embodiment will be described by way of example.

The ultrasound imaging apparatus 100b of the present embodiment has basically the same configuration as the ultrasound imaging apparatus 100 of the first embodiment. In addition, in order to accept the adjustment from the user (operator) as described above, it is further provided with a configuration for implementing this processing. In the following, the present embodiment will be described focusing on the configuration which is different from the first embodiment.

Figure 17:
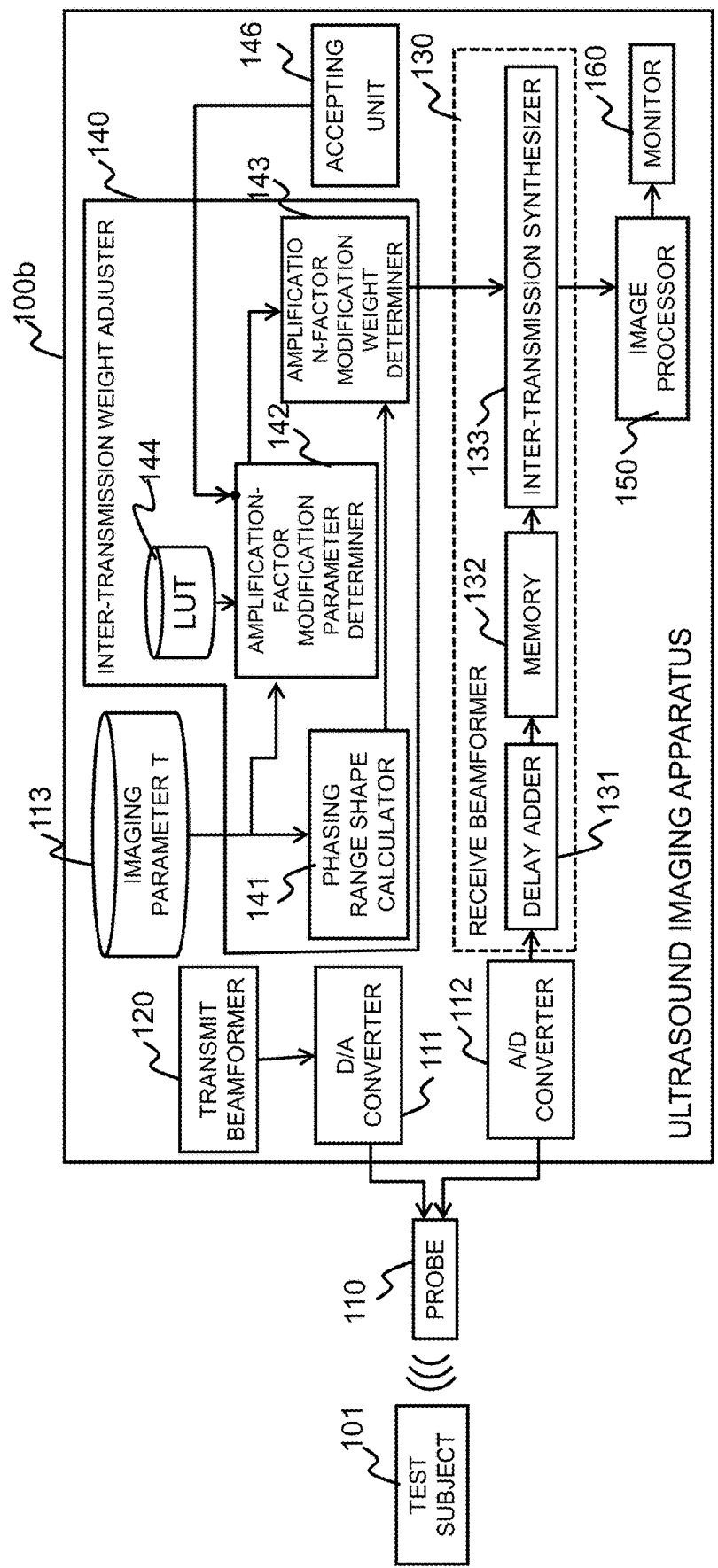
FIG. 17 is a functional block diagram of the ultrasound imaging apparatus according to a third embodiment.

As shown in FIG. 17, in order to accept further adjustment from the user, in the present embodiment, there is provided an accepting unit 146 for accepting user's adjustment of the weight adjustment parameter, in addition to the configuration of the ultrasound imaging apparatus 100 according to the first embodiment. The processing performed in the amplification-factor modification parameter determiner 142 is different from the first embodiment.

The amplification-factor modification parameter determiner 142 of the present embodiment initially reads the inclined strength accumulated in the LUT 144 in association with the imaging conditions, similar to the first embodiment, and the inclined strength is determined as the weight adjustment parameter. Thereafter, upon accepting an adjustment from the user via the accepting unit 146, the adjustment parameter is adjusted according to this accepted adjustment, and the weight adjustment parameter thus adjusted is determined as the weight adjustment parameter to be outputted.

The accepting unit 146 accepts the adjustment of the inclined strength from the user. FIG. 18(a) illustrates a GUI screen example (parameter acceptance screen) that the accepting unit 146 displays on the monitor 160, and this GUI screen is used for accepting the adjustment of inclined strength from the user.

As illustrated, the parameter acceptance screen 600 is provided with an image display area 610, a parameter acceptance area 620, and an OK button 630. In the image display area 610, an ultrasound image is displayed, which is generated by the receive beamformer 130 and the image processor 150, on the basis of the weight adjustment parameter determined by the amplification-factor modification parameter determiner 142. The parameter acceptance area 620 is an area for accepting the adjustment of the weight adjustment parameter by the user. The OK button 630 is a button for accepting the user's intention of approving the inter-transmission weight that is presently adjusted.

In the present embodiment, there will be described an example where adjustment of the inclined strength is accepted, as one of the weight adjustment parameters. By way of example, as illustrated in FIG. 18(a), a slider 621 with division of a scale is displayed, together with a knob 622. The user moves the knob 622 along the slider 621, thereby instructing adjustment of the inclined strength. In the initial stage, the knob 622 is displayed at the position indicating the inclined strength when the ultrasound image displayed in the image display area 610 is generated.

A changeable range of the inclined strength is preset according to the imaging conditions, and it is held in the LUT 144. The changeable range of the inclined strength may vary with respect to each transmission and reception, or with respect to each position of the phasing range in the transmission direction every transmission and reception.

It should be noted that the OK button 630 is not necessarily provided. It is also possible configure such that current parameter is determined as approved, if there is no instruction of adjustment from the user for a certain period of time. An interface used for accepting adjustment of the inclined strength from the user may be displayed within the screen by pressing a GUI display changeover switch, or instead of displaying in the screen, a button or a dial on a control panel may be used as the interface.

[Process Flow of Ultrasound Imaging]

Figure 19:
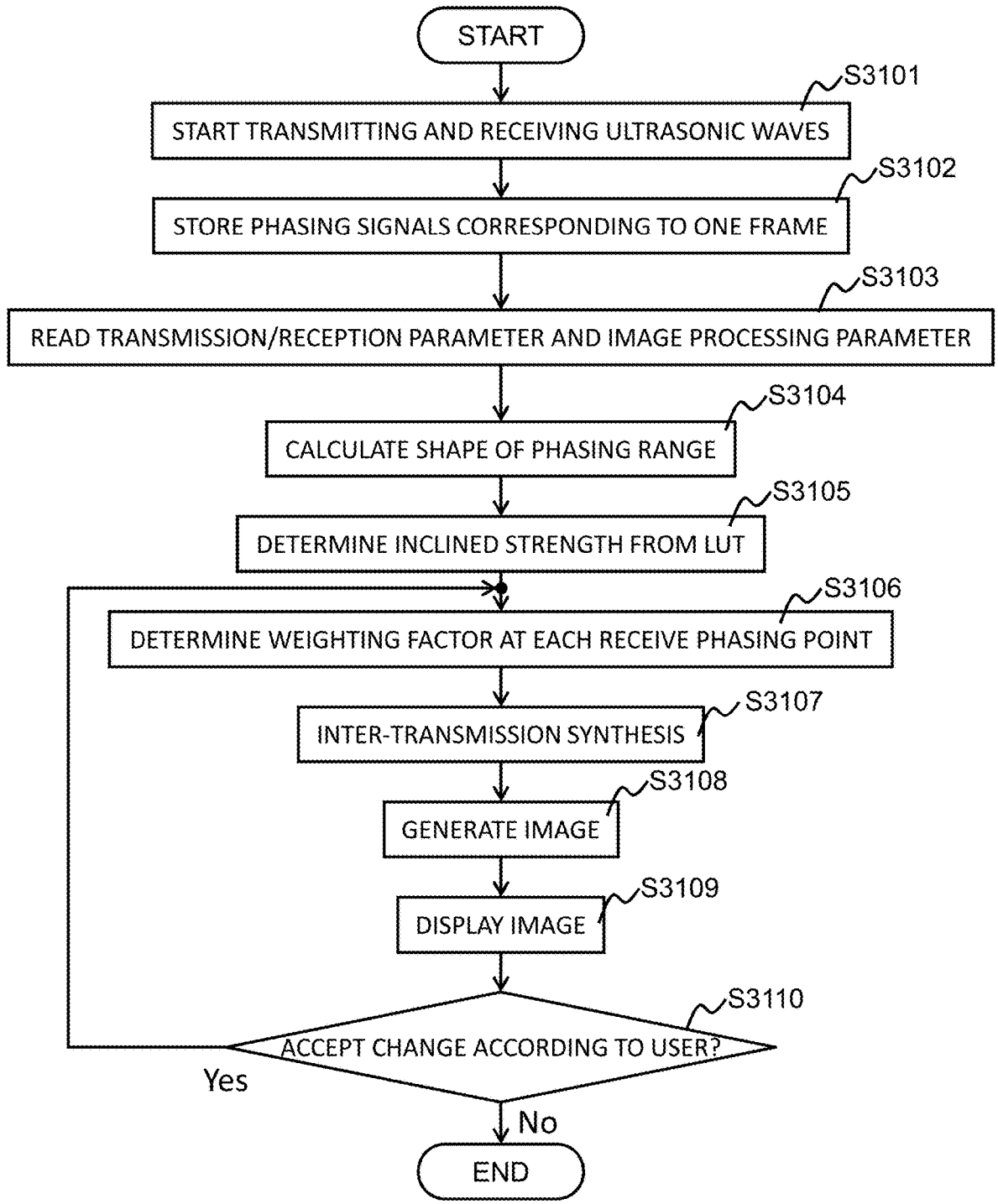
FIG. 19 is a flowchart showing the ultrasound imaging process according to the third embodiment.

With reference to FIG. 19, the ultrasound imaging process flow of the present embodiment will be described. When a user sets various imaging conditions, parameters, and the like, and instructs to initiate the process, the following process is started.

According to the imaging conditions set by the user, the transmit beamformer 120 is activated, ultrasonic waves are transmitted from the probe 110, and transmission and reception are started (step S3101).

The delay adder 131 of the receive beamformer 130 obtains phasing signals at each receive phasing point 202 every transmission, repeats accumulating the signals in the memory 132, and then obtains phasing signals corresponding to one frame (step S3102).

The inter-transmission weight adjuster 140 reads the transmit-receive parameter and the processing parameter from the imaging parameter table 113 (step S3103). Then, the phasing range shape calculator 141 calculates the shape of the phasing range 200, according to the imaging conditions, parameters, and the like (step S3104). The amplification-factor modification parameter determiner 142 retrieves inclined strength from the LUT 144 (step S3105).

The amplification-factor modification weight determiner 142 adjusts the inter-transmission weight shape 400, and according to the adjustment, determines the weighting factor 410 at each receiving phasing point every transmission and reception (step S3106).

The inter-transmission synthesizer 133 multiplies the signals at each receive phasing point 202 every transmission and reception, by the weighting factor 410 determined according to the adjusted inter-transmission weight shape 400, and performs the inter-transmission synthesis (step S3107).

The image processor 150 generates an image from a group of the phasing signals after the inter-transmission synthesis is performed (step S3108), and displays the image on the monitor 160 (step S3109). In the present embodiment, the image is displayed on the parameter acceptance screen 600.

When the accepting unit 146 accepts the adjustment of inclined strength from the user via the parameter acceptance area 620 (step S3110), the amplification-factor modification parameter determiner 142 adjusts the inclined strength according to thus accepted adjustment, and provides a notification to the amplification-factor modification weight determiner 143. Then, the amplification-factor modification weight determiner 142 shifts the processing to the step S3106, and determines the weighting factor again by using the inclined strength received from the accepting unit 146.

On the other hand, in the step S3110, if the OK button is pressed by the user without accepting the change of the inclined strength, the accepting unit 146 completes the processing.

As described so far, the ultrasound imaging apparatus 100b of the present embodiment is provided with, similar to the first embodiment, the probe 110, the transmit beamformer 120, the receive beamformer 130, the inter-transmission weight adjuster 140, and the image processor 150. Then, the inter-transmission weight adjuster 140 may adjust the inter-transmission weight, in such a manner that the amplification factor difference between the adjacent receive phasing points 202 is reduced, as to each receive phasing point 202 after the inter-transmission synthesis is performed. In addition, the inter-transmission weight adjuster 140 may be provided with the phasing range shape calculator 141, the amplification-factor modification parameter determiner 142, and the amplification-factor modification weight determiner 143.

Further, the ultrasound imaging apparatus 100b may further be provided with the accepting unit 146 for accepting an entry of the weight adjustment parameter from a user, and the amplification-factor modification parameter determiner 142 may adjust the weight adjustment parameter according to the adjustment thus accepted.

As described above, according to the present embodiment, similar to the aforementioned embodiments, it is possible to obtain smooth variation of the amplification factor of the receive phasing points in the image after the inter-transmission synthesis is performed. Since the image is generated from such group of phasing signals, it is possible to obtain the image with less artifacts.

Further according to the present embodiment, the user is allowed to adjust the weight adjustment parameter to suit to the preferences of the user. Therefore, an image with a desired quality can be obtained.

The embodiments have been described so far, taking the example that the LUT 144 is provided and the initial weight adjustment parameter is acquired from the LUT 144, but this is not the only example. By way of example, it is possible to configure such that a predetermined value is used, or the initial value and the amount of change of the weight adjustment parameter are held, so as to search for an optimum weight adjustment parameter as described in the second embodiment. In this case, the image determined by the search is presented to the user so as to accept adjustment of the weight adjustment parameter.

<Modification Example of Weight Adjustment Parameter>

Each of the aforementioned embodiments has been described, taking the example that the weighting factor 410 by which each receive phasing point 202 is multiplied is set to a value from 0 to 1. However, the value range of the weighting factor 410 is not limited to this example. The value may fall into the range from 1 to 2, from 0.5 to 1, from 0 to −1, or the like. Alternatively, it may be a value that renders the maximum value of the amplification factor for the inter-transmission synthesis to be 1.

It is further possible to determine the maximum value of the weighting factor 410, inversely proportional to the width of the phasing range 200 in the vertical direction. By way of example, the value is determined in such a manner that when the maximum value of the weighting factor 410 at the position of a certain width is assumed as 1, the maximum value of the weighting factor 410 at the position with double width becomes 0.5. Alternatively, the weighting factor 410 is determined to be a numerical value that renders a distribution of the amplification factor to be homogeneous after performing the inter-transmission synthesis for all the transmissions constituting one frame.

In addition, in the second embodiment, the weighting factor 410 may also be targeted for searching. In this case, an initial value, the amount of change, and a threshold are held in advance, and searching is performed in the similar method as described above, thereby determining an optimum value.

Further, the third embodiment may be configured in such a manner that the weighting factor 410 may also be designated via the parameter acceptance screen 600.

FIG. 18(b) illustrates an example of the parameter acceptance screen 601 for the case above. The parameter acceptance area 640 in the parameter acceptance screen 601 may further accept settings of a gain of the weighting factor 410. Specifically, a two-dimensional slider 641 is displayed as shown in FIG. 18(b), and designation of the inclined strength and the gain of the weighting factor 410 is accepted by moving the knobs 642.

The parameter acceptance area 640 may be configured such that when the user designates the gain of the weighting factor and the inclined strength, a cross section of the weight distribution shape is displayed. Displayed ranges for respective values are predefined.

<Modification Example of Phasing Range>

In each of the embodiments above, the phasing range 200 is defined according to a type of the probe 110, a position of the element used for transmission, a position where the transmitted sound waves are focused, and transmit-receive parameters including the shape of transmission beam. However, definitions of the phasing range 200 are not limited to those as described above. By way of example, an image creating method may also be considered.

By way of example, as shown in FIG. 20(a), it is known that in the image creating method, using harmonics with frequency components being integral multiple of a transmission frequency, a transmission sound field is reduced more, in particular, at a point deeper from the transmission focused point as shown in FIG. 20(c), compared to the case where the transmission frequency as shown in FIG. 20(b) is used.

The phasing range may also be defined without depending on the transmission sound field.

In the aforementioned embodiments, the ultrasound imaging apparatuses 100, 100a, and 100b are provided with a CPU, a memory, and a storage unit. Functions of the ultrasound imaging apparatus 100, 100a, and 100b are implemented when the CPU loads programs stored in the storage unit into the memory, and executes the programs. All or a part of the functions may be implemented by hardware such as ASIC (Application Specific Integrated Circuit) and FPGA.

Various data used for processing in each function, and various data generated during the processing are stored in the storage unit. For example, the imaging parameter table 113 and the LUT 144 are constructed in the storage unit.

DESCRIPTION OF SYMBOLS

100: ultrasound imaging apparatus, 100a: ultrasound imaging apparatus, 100b: ultrasound imaging apparatus, 101: test subject, 110: probe, 111: D/A converter, 112: A/D converter, 113: imaging parameter table, 120: transmit beamformer, 130: receive beamformer, 131: delay adder, 132: memory, 133: inter-transmission synthesizer, 140: inter-transmission weight adjuster, 141: phasing range shape calculator, 142: amplification-factor modification parameter determiner, 143: amplification-factor modification weight determiner, 144: LUT, 145: verification unit, 146: accepting unit, 150: image processor, 160: monitor, 200: phasing range, 201: receive scanning line, 202: receive phasing point, 210: imaging range, 211: central receive scanning line, 310: inter-transmission synthesis amplification-factor distribution, 311: receive scanning line, 320: amplification factor, 321: amplification factor, 400: inter-transmission weight shape, 401: inter-transmission weight shape, 402: inter-transmission weight shape, 403: inter-transmission weight shape, 410: weighting factor, 411: weighting factor, 421: negative side end, 422: positive side end, 511: point image, 512: result, 521: point image, 522: point image, 600: parameter acceptance screen, 601: parameter acceptance screen, 610: image display area, 620: parameter acceptance area, 621: slider, 622: knob, 630: OK button, 640: parameter acceptance area, 641: slider, 642: knob, 701: imaging condition, 702: weight adjustment parameter.

What is claimed is:

1. An ultrasound imaging apparatus comprising,
a probe provided with an array of plural ultrasound elements;
a transmit beamformer configured to transmit ultrasonic waves to a test subject from at least a part of the array of plural ultrasound elements, and apply a delay time to the ultrasonic waves transmitted respectively from the ultrasound elements of the part of the array of plural ultrasound elements, so as to focus the ultrasonic waves on a predetermined depth; and
a receive beamformer comprising:
a delay adder configured to delay received signals outputted from the plural ultrasound elements that receive ultrasonic waves from the test subject, and add the delayed received signals together, thereby phasing the received signals to obtain obtaining a phasing signal as to each of plural receive phasing points within a predetermined phasing range; and
an inter-transmission synthesizer configured to multiply, by an inter-transmission weight, a plurality of the phasing signals obtained through plural transmissions and receptions at each of the receive phasing points, and then to combine the phasing signals so as to perform inter-transmission synthesis;
an inter-transmission weight adjuster configured to adjust the inter-transmission weight in accordance with the phasing range; and
an image processor configured to generate an ultrasound image from the phasing signals, after the inter-transmission synthesis is performed as to the plural receive phasing points,
wherein the inter-transmission weight adjuster adjusts the inter-transmission weight in such a manner that a difference in magnitude of amplification factors of the receive phasing points that are adjacent is reduced, as to each of the receive phasing points after the inter-transmission synthesis is performed, the amplification factors indicating an amplification amount of receive phasing points based on a number of times each receive phasing point is included in the phasing range.

2. The ultrasound imaging apparatus according to claim 1, wherein,
the inter-transmission weight adjuster comprises:
a phasing range shape calculator configured to calculate a shape of the phasing range every transmission and reception;
an amplification-factor modification parameter determiner configured to determine a weight adjustment parameter for specifying a variation form of values of the inter-transmission weight being adjusted, within the phasing range; and
an amplification-factor modification weight determiner configured to determine the inter-transmission weight being adjusted, according to the phasing range and the weight adjustment parameter.

3. The ultrasound imaging apparatus according to claim 2, wherein,
the weight adjustment parameter is represented by inclined strength of a predefined function.

4. The ultrasound imaging apparatus according to claim 2, wherein,
the weight adjustment parameter is represented by a minimum value and a maximum value of the inter-transmission weight.

5. The ultrasound imaging apparatus according to claim 2, further comprising:
a lookup table configured to hold values of the weight adjustment parameter in association with imaging conditions, wherein,
the amplification-factor modification parameter determiner acquires the value of the weight adjustment parameter from the lookup table.

6. The ultrasound imaging apparatus according to claim 2, wherein,
the inter-transmission weight adjuster further comprises a verification unit configured to verify suitability of the inter-transmission weight that is determined by the amplification-factor modification weight determiner, and
when the inter-transmission weight is determined as inappropriate, the amplification-factor modification parameter determiner changes the value of the weight adjustment parameter, by a predetermined amount of change.

7. The ultrasound imaging apparatus according to claim 2, further comprising:
an accepting unit configured to accept adjustment of the weight adjustment parameter from a user, wherein,
the amplification-factor modification parameter determiner adjusts the weight adjustment parameter in accordance with the adjustment being accepted.

8. The ultrasound imaging apparatus according to claim 1, wherein,
the inter-transmission weight is adjusted in such a manner that a value of the receive phasing point is maximized at the center of the phasing range, with respect to a direction orthogonal to a transmission direction, and the value is decreased along with moving away from the center.

9. The ultrasound imaging apparatus according to claim 7, wherein,
the accepting unit displays a parameter acceptance screen comprising an image display area configured to display an ultrasound image generated according to the weight adjustment parameter that is determined by the amplification-factor modification parameter determiner, and a parameter acceptance area configured to accept the adjustment of the weight adjustment parameter, and
the accepting unit accepts the adjustment of the weight adjustment parameter via the parameter acceptance screen.

10. An ultrasound imaging apparatus comprising,
a probe provided with an array of plural ultrasound elements;
a transmit beamformer configured to transmit ultrasonic waves to a test subject from at least a part of the array of plural ultrasound elements, and apply a delay time to the ultrasonic waves transmitted respectively from the ultrasound elements of the part of the array of plural ultrasound elements, so as to focus the ultrasonic waves on a predetermined depth; and
a receive beamformer comprising:
a delay adder configured to delay received signals outputted from the plural ultrasound elements that receive ultrasonic waves from the test subject, and add the delayed received signals together, thereby phasing the received signals to obtain obtaining a phasing signal as to each of plural receive phasing points within a predetermined phasing range; and
an inter-transmission synthesizer configured to multiply, by an inter-transmission weight, a plurality of the phasing signals obtained through plural transmissions and receptions at each of the receive phasing points, and then to combine the phasing signals so as to perform inter-transmission synthesis;
an inter-transmission weight adjuster configured to adjust the inter-transmission weight in accordance with the phasing range; and
an image processor configured to generate an ultrasound image from the phasing signals, after the inter-transmission synthesis is performed as to the plural receive phasing points,
wherein the inter-transmission weight adjuster comprises:
a phasing range shape calculator configured to calculate a shape of the phasing range every transmission and reception;
an amplification-factor modification parameter determiner configured to determine a weight adjustment parameter for specifying a variation form of values of the inter-transmission weight being adjusted, within the phasing range; and
an amplification-factor modification weight determiner configured to determine the inter-transmission weight being adjusted, according to the phasing range and the weight adjustment parameter,
wherein the inter-transmission weight adjuster further comprises a verification unit configured to verify suitability of the inter-transmission weight that is determined by the amplification-factor modification weight determiner,
wherein when the inter-transmission weight is determined as inappropriate, the amplification-factor modification parameter determiner changes the value of the weight adjustment parameter, by a predetermined amount of change, and
wherein the verification unit determines as inappropriate, a result of the inter-transmission synthesis of the inter-transmission weight of every transmission and reception, when a maximum value of a weight value ratio between the receive phasing points being adjacent is larger than a predetermined threshold.

11. The ultrasound imaging apparatus according to claim 1, wherein,
the phasing range is defined every transmission, in conformity with transmitted sound waves.

12. A method in an ultrasound imaging apparatus, comprising the steps of:
transmitting ultrasonic waves to a test subject, and applying a delay time to the ultrasonic waves transmitted respectively from a plurality of ultrasound elements, so as to focus the ultrasonic waves on a predetermined depth;
delaying received signals outputted from the plural ultrasound elements that receive ultrasonic waves from the test subject, and adding the delayed received signals together, thereby phasing the received signals to obtain obtaining a phasing signal as to each of plural receive phasing points within a predetermined phasing range; and
multiplying, by an inter-transmission weight, a plurality of the phasing signals obtained through plural transmissions and receptions at each of the receive phasing points, and then combining the phasing signals so as to perform inter-transmission synthesis;
adjusting the inter-transmission weight in accordance with the phasing range; and
generating an ultrasound image from the phasing signals, after the inter-transmission synthesis is performed as to the plural receive phasing points;
calculating a shape of a predetermined phasing range; and
adjusting the inter-transmission weight being a set of weighting factors by which phasing signals at respective receive phasing points are multiplied when aperture synthesis is performed, in accordance with the shape of the phasing range,
wherein the inter-transmission weight is adjusted in such a manner that a difference in magnitude of amplification factors of the receive phasing points that are adjacent is reduced, as to each of the receive phasing points after the inter-transmission synthesis is performed, the amplification factors indicating an amplification amount of receive phasing points based on a number of times each receive phasing point is included in the phasing range.

13. The method of adjusting the inter-transmission weight according to claim 12, comprising,
applying the inter-transmission weight adjusted by the method according to claim 12, to the phasing signals at the respective receive phasing points obtained every transmission and reception,
performing inter-transmission synthesis thereon, and
generating an image from the phasing signals after the inter-transmission synthesis is performed.

* * * * *